(12) United States Patent
Childress et al.

(10) Patent No.: US 12,233,197 B2
(45) Date of Patent: Feb. 25, 2025

(54) BLOCKAGE AND CANISTER FULL DETECTION IN REDUCED PRESSURE THERAPY SYSTEMS

(71) Applicant: Smith & Nephew, Inc., Memphis, TN (US)

(72) Inventors: Carrie Lee Childress, Dallas, TX (US); William Joseph Jaecklein, Saint Petersburg, FL (US); Felix C. Quintanar, Hull (GB)

(73) Assignee: Smith & Nephew, Inc., Memphis, TN (US)

(*) Notice: Subject to any disclaimer, the term of this patent is extended or adjusted under 35 U.S.C. 154(b) by 1038 days.

(21) Appl. No.: 17/167,519

(22) Filed: Feb. 4, 2021

(65) Prior Publication Data

US 2021/0252208 A1 Aug. 19, 2021

Related U.S. Application Data

(63) Continuation of application No. 16/219,641, filed on Dec. 13, 2018, now Pat. No. 10,912,870, which is a
(Continued)

(51) Int. Cl.
*A61M 1/00* (2006.01)
*A61F 13/05* (2024.01)

(52) U.S. Cl.
CPC ............ *A61M 1/96* (2021.05); *A61F 13/05* (2024.01); *A61M 1/60* (2021.05); *A61M 1/732* (2021.05);
(Continued)

(58) Field of Classification Search
CPC ... A61F 13/05; A61M 1/982; A61M 2205/15; A61M 2205/18; A61M 2205/3331;
(Continued)

(56) References Cited

U.S. PATENT DOCUMENTS

| 695,270 A | 3/1902 | Beringer |
| 3,194,239 A | 7/1965 | Sullivan et al. |

(Continued)

FOREIGN PATENT DOCUMENTS

| CA | 2819475 A1 | 6/2012 |
| CN | 104721892 A | 6/2015 |

(Continued)

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 p.
(Continued)

*Primary Examiner* — Ariana Zimbouski
(74) *Attorney, Agent, or Firm* — Knobbe, Martens, Olson & Bear, LLP

(57) ABSTRACT

Embodiments of negative pressure wound therapy apparatuses and methods for using such apparatuses are disclosed. In some embodiments, a negative pressure wound therapy apparatus includes a controller configured to determine a level of exudate in a canister (or a dressing) based at least in part on one or more characteristics of pressure signals generated by a negative pressure source and monitored by a pressure sensor. One such characteristic of the pressure signals can be amplitude, which may increase as a level of exudate in the canister (or dressing) increases. The canister (or dressing) can include a filter configured to become occluded in order to prevent overflow of the canister (or dressing). The controller can be additionally configured to detect and indicate a canister (or dressing) pre-full condition before the filter becomes occluded. More efficient and reliable operation of the negative pressure wound therapy apparatus can thereby be attained.

20 Claims, 14 Drawing Sheets

Related U.S. Application Data continuation of application No. 14/912,071, filed as application No. PCT/US2014/050233 on Aug. 7, 2014, now Pat. No. 10,155,070.

(60) Provisional application No. 61/865,516, filed on Aug. 13, 2013.

(52) U.S. Cl.
CPC .............. *A61M 1/78* (2021.05); *A61M 1/982* (2021.05); *A61M 1/882* (2021.05); *A61M 2205/15* (2013.01); *A61M 2205/18* (2013.01); *A61M 2205/3331* (2013.01); *A61M 2205/3344* (2013.01); *A61M 2205/3382* (2013.01); *A61M 2205/75* (2013.01)

(58) Field of Classification Search
CPC .. A61M 2205/3344; A61M 2205/3382; A61M 2205/75
See application file for complete search history.

(56) References Cited

U.S. PATENT DOCUMENTS

| | | |
|---|---|---|
| 4,832,299 A | 5/1989 | Gorton et al. |
| 5,158,528 A | 10/1992 | Walker et al. |
| 5,174,533 A | 12/1992 | Pryor et al. |
| 5,215,523 A | 6/1993 | Williams et al. |
| 5,219,428 A | 6/1993 | Stern |
| 5,419,768 A | 5/1995 | Kayser |
| 5,449,347 A | 9/1995 | Preen et al. |
| 5,466,229 A | 11/1995 | Elson et al. |
| 5,473,536 A | 12/1995 | Wimmer |
| 5,582,601 A | 12/1996 | Wortrich et al. |
| 5,584,824 A | 12/1996 | Gillette et al. |
| 5,599,308 A | 2/1997 | Krupa |
| 5,622,429 A | 4/1997 | Heinze |
| 5,656,027 A | 8/1997 | Ellingboe |
| 5,669,892 A | 9/1997 | Keogh et al. |
| 5,687,717 A | 11/1997 | Halpern et al. |
| 5,693,013 A | 12/1997 | Geuder |
| 5,779,207 A | 7/1998 | Danby |
| D408,625 S | 4/1999 | Barker |
| 5,956,023 A | 9/1999 | Lyle et al. |
| 5,989,234 A | 11/1999 | Valerio et al. |
| 6,174,306 B1 | 1/2001 | Fleischmann |
| 6,228,056 B1 | 5/2001 | Boehringer et al. |
| 6,241,739 B1 | 6/2001 | Waldron |
| 6,250,482 B1 | 6/2001 | Want et al. |
| 6,572,530 B1 | 6/2003 | Araki et al. |
| 6,574,518 B1 | 6/2003 | Lounsberry et al. |
| 6,605,032 B2 | 8/2003 | Benkowski et al. |
| 6,640,246 B1 | 10/2003 | Gary et al. |
| 6,681,003 B2 | 1/2004 | Linder et al. |
| 6,738,052 B1 | 5/2004 | Manke et al. |
| 7,004,915 B2 | 2/2006 | Boynton et al. |
| 7,022,113 B2 | 4/2006 | Lockwood et al. |
| 7,128,735 B2 | 10/2006 | Weston |
| D565,177 S | 3/2008 | Locke et al. |
| 7,361,184 B2 | 4/2008 | Joshi |
| D581,042 S | 11/2008 | Randolph et al. |
| D581,522 S | 11/2008 | Randolph et al. |
| D590,934 S | 4/2009 | Randolph et al. |
| 7,553,306 B1 | 6/2009 | Hunt et al. |
| 7,569,742 B2 | 8/2009 | Haggstrom et al. |
| 7,594,901 B2 | 9/2009 | Hopkins et al. |
| D602,582 S | 10/2009 | Pidgeon et al. |
| D602,583 S | 10/2009 | Pidgeon et al. |
| 7,598,855 B2 | 10/2009 | Scalisi et al. |
| 7,611,500 B1 | 11/2009 | Lina et al. |
| 7,615,036 B2 | 11/2009 | Joshi et al. |
| 7,699,823 B2 | 4/2010 | Haggstrom et al. |
| 7,723,560 B2 | 5/2010 | Lockwood et al. |
| 7,753,894 B2 | 7/2010 | Blott et al. |
| 7,770,855 B2 | 8/2010 | Locke et al. |
| 7,776,028 B2 | 8/2010 | Miller et al. |
| D625,801 S | 10/2010 | Pidgeon et al. |
| 7,846,141 B2 | 12/2010 | Weston |
| 7,857,806 B2 | 12/2010 | Karpowicz et al. |
| 7,883,494 B2 | 2/2011 | Martin |
| 7,890,887 B1 | 2/2011 | Linardos et al. |
| D635,588 S | 4/2011 | Sprules |
| 7,925,603 B1 | 4/2011 | Laidig et al. |
| 7,927,319 B2 | 4/2011 | Lawhorn |
| 7,933,817 B2 | 4/2011 | Radl et al. |
| 7,945,452 B2 | 5/2011 | Fathallah et al. |
| D644,250 S | 8/2011 | Barber et al. |
| 7,988,850 B2 | 8/2011 | Roncadi et al. |
| 8,007,481 B2 | 8/2011 | Schuessler et al. |
| 8,048,046 B2 | 11/2011 | Hudspeth et al. |
| 8,061,360 B2 | 11/2011 | Locke et al. |
| 8,066,243 B2 | 11/2011 | Svedman et al. |
| 8,096,515 B2 | 1/2012 | Locke et al. |
| 8,100,873 B2 | 1/2012 | Jaeb et al. |
| 8,105,295 B2 | 1/2012 | Blott et al. |
| 8,216,198 B2 | 7/2012 | Heagle et al. |
| 8,228,188 B2 | 7/2012 | Key et al. |
| 8,235,955 B2 | 8/2012 | Blott et al. |
| 8,240,470 B2 | 8/2012 | Pidgeon et al. |
| 8,246,607 B2 | 8/2012 | Karpowicz et al. |
| 8,257,328 B2 | 9/2012 | Augustine et al. |
| 8,267,918 B2 | 9/2012 | Johnson et al. |
| 8,294,586 B2 | 10/2012 | Pidgeon et al. |
| 8,298,200 B2 | 10/2012 | Vess et al. |
| 8,308,714 B2 | 11/2012 | Weston et al. |
| 8,317,752 B2 | 11/2012 | Cozmi et al. |
| 8,333,744 B2 | 12/2012 | Hartwell et al. |
| 8,360,975 B1 | 1/2013 | Schwieterman et al. |
| 8,366,692 B2 | 2/2013 | Weston et al. |
| 8,377,016 B2 | 2/2013 | Argenta et al. |
| 8,377,018 B2 | 2/2013 | Bendele et al. |
| 8,400,295 B1 | 3/2013 | Khaira |
| 8,403,902 B2 | 3/2013 | Locke et al. |
| 8,409,170 B2 | 4/2013 | Locke et al. |
| 8,424,517 B2 | 4/2013 | Sutherland et al. |
| 8,439,882 B2 | 5/2013 | Kelch |
| 8,444,392 B2 | 5/2013 | Turner et al. |
| 8,480,641 B2 | 7/2013 | Jacobs |
| 8,494,349 B2 | 7/2013 | Gordon |
| 8,535,296 B2 | 9/2013 | Blott et al. |
| 8,540,688 B2 | 9/2013 | Eckstein et al. |
| 8,552,880 B2 | 10/2013 | Kopp et al. |
| 8,558,964 B2 | 10/2013 | Bedingfield |
| 8,604,265 B2 | 12/2013 | Locke et al. |
| 8,617,129 B2 | 12/2013 | Hartwell |
| 8,622,981 B2 | 1/2014 | Hartwell et al. |
| 8,626,342 B2 | 1/2014 | Williams et al. |
| 8,628,258 B2 | 1/2014 | Vogt |
| 8,641,693 B2 | 2/2014 | Locke et al. |
| 8,652,111 B2 | 2/2014 | Pratt et al. |
| 8,668,677 B2 | 3/2014 | Eckstein et al. |
| 8,694,600 B2 | 4/2014 | Gaines et al. |
| 8,747,376 B2 | 6/2014 | Locke et al. |
| 8,756,078 B2 | 6/2014 | Collins et al. |
| 8,771,259 B2 | 7/2014 | Karpowicz et al. |
| 8,791,316 B2 | 7/2014 | Greener |
| 8,798,284 B2 | 8/2014 | Cartwright et al. |
| 8,814,841 B2 | 8/2014 | Hartwell |
| 8,814,842 B2 | 8/2014 | Coulthard et al. |
| 8,827,983 B2 | 9/2014 | Braga et al. |
| 8,843,327 B2 | 9/2014 | Vernon-Harcourt et al. |
| 8,845,603 B2 | 9/2014 | Middleton et al. |
| 8,845,604 B2 | 9/2014 | Croizat et al. |
| 8,852,149 B2 | 10/2014 | Weston et al. |
| 8,858,517 B2 | 10/2014 | Pan et al. |
| 8,870,812 B2 | 10/2014 | Alberti et al. |
| 8,897,198 B2 | 11/2014 | Gaines et al. |
| 8,902,278 B2 | 12/2014 | Pinter et al. |
| 8,905,959 B2 | 12/2014 | Basaglia |
| 8,905,985 B2 | 12/2014 | Allen et al. |
| 8,926,574 B2 | 1/2015 | Croizat et al. |
| 8,943,168 B2 | 1/2015 | Wiesner et al. |
| 8,945,030 B2 | 2/2015 | Weston |
| 8,945,073 B2 | 2/2015 | Croizat et al. |

(56) References Cited

U.S. PATENT DOCUMENTS

| | | |
|---|---|---|
| 8,945,074 B2 | 2/2015 | Buan et al. |
| 8,961,497 B2 | 2/2015 | Ryu et al. |
| 8,974,429 B2 | 3/2015 | Gordon et al. |
| 9,017,286 B2 | 4/2015 | Kamen et al. |
| 9,019,681 B2 | 4/2015 | Locke et al. |
| 9,023,002 B2 | 5/2015 | Robinson et al. |
| 9,058,634 B2 | 6/2015 | Buan et al. |
| 9,067,003 B2 | 6/2015 | Buan et al. |
| 9,084,845 B2 | 7/2015 | Adie et al. |
| 9,220,822 B2 | 12/2015 | Hartwell |
| 10,537,657 B2 | 1/2020 | Phillips et al. |
| 2001/0013822 A1 | 8/2001 | Nazarian et al. |
| 2001/0031944 A1 | 10/2001 | Peterson et al. |
| 2001/0041831 A1 | 11/2001 | Starkweather et al. |
| 2001/0049609 A1 | 12/2001 | Girouard et al. |
| 2002/0002326 A1 | 1/2002 | Causey et al. |
| 2002/0002368 A1 | 1/2002 | Tomita et al. |
| 2002/0013516 A1 | 1/2002 | Freyre et al. |
| 2002/0015034 A1 | 2/2002 | Malmborg |
| 2002/0026160 A1 | 2/2002 | Takahashi et al. |
| 2002/0049562 A1 | 4/2002 | Hahn |
| 2002/0065685 A1 | 5/2002 | Sasaki et al. |
| 2002/0082568 A1 | 6/2002 | Yam |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0161317 A1 | 10/2002 | Risk et al. |
| 2002/0193679 A1 | 12/2002 | Malave et al. |
| 2002/0198505 A1 | 12/2002 | Want et al. |
| 2003/0009244 A1 | 1/2003 | Engleson et al. |
| 2003/0018395 A1 | 1/2003 | Crnkovich et al. |
| 2003/0018736 A1 | 1/2003 | Christ et al. |
| 2003/0028175 A1 | 2/2003 | D'Antonio |
| 2003/0040687 A1 | 2/2003 | Boynton et al. |
| 2003/0093041 A1 | 5/2003 | Risk, Jr. et al. |
| 2003/0105389 A1 | 6/2003 | Noonan et al. |
| 2003/0105649 A1 | 6/2003 | Sheiner et al. |
| 2003/0128125 A1 | 7/2003 | Burbank et al. |
| 2003/0164600 A1 | 9/2003 | Dunn et al. |
| 2003/0176183 A1 | 9/2003 | Drucker et al. |
| 2003/0182158 A1 | 9/2003 | Son |
| 2003/0214412 A1 | 11/2003 | Ho et al. |
| 2003/0221687 A1 | 12/2003 | Kaigler |
| 2003/0229518 A1 | 12/2003 | Abraham-Fuchs et al. |
| 2003/0233071 A1 | 12/2003 | Gillespie et al. |
| 2004/0019464 A1 | 1/2004 | Martucci et al. |
| 2004/0033140 A1 | 2/2004 | Jensen et al. |
| 2004/0039255 A1 | 2/2004 | Simonsen et al. |
| 2004/0054338 A1 | 3/2004 | Bybordi et al. |
| 2004/0054775 A1 | 3/2004 | Poliac et al. |
| 2004/0059284 A1 | 3/2004 | Nash et al. |
| 2004/0064132 A1 | 4/2004 | Boehringer et al. |
| 2004/0078223 A1 | 4/2004 | Sacco et al. |
| 2004/0102743 A1 | 5/2004 | Walker |
| 2004/0120825 A1 | 6/2004 | Bouton et al. |
| 2004/0143458 A1 | 7/2004 | Pulkkinen et al. |
| 2004/0158193 A1 | 8/2004 | Bui et al. |
| 2004/0171982 A1 | 9/2004 | Danchin |
| 2004/0176983 A1 | 9/2004 | Birkett et al. |
| 2004/0181314 A1 | 9/2004 | Zaleski |
| 2004/0193449 A1 | 9/2004 | Wildman et al. |
| 2004/0227737 A1 | 11/2004 | Novak et al. |
| 2004/0249673 A1 | 12/2004 | Smith |
| 2005/0011282 A1 | 1/2005 | Voege et al. |
| 2005/0022274 A1 | 1/2005 | Campbell et al. |
| 2005/0033124 A1 | 2/2005 | Kelly et al. |
| 2005/0060211 A1 | 3/2005 | Xiao et al. |
| 2005/0065471 A1 | 3/2005 | Kuntz |
| 2005/0114176 A1 | 5/2005 | Dominick et al. |
| 2005/0116126 A1 | 6/2005 | Ugent et al. |
| 2005/0119914 A1 | 6/2005 | Batch |
| 2005/0124966 A1 | 6/2005 | Karpowicz et al. |
| 2005/0187528 A1 | 8/2005 | Berg |
| 2005/0209560 A1 | 9/2005 | Boukhny et al. |
| 2005/0230575 A1 | 10/2005 | Zelenski et al. |
| 2005/0240111 A1 | 10/2005 | Chung |
| 2005/0256447 A1 | 11/2005 | Richardson et al. |
| 2005/0261805 A1 | 11/2005 | Mori et al. |
| 2005/0283382 A1 | 12/2005 | Donoghue et al. |
| 2006/0029675 A1 | 2/2006 | Ginther |
| 2006/0064491 A1 | 3/2006 | Ebert et al. |
| 2006/0089544 A1 | 4/2006 | Williams et al. |
| 2006/0095853 A1 | 5/2006 | Amyot et al. |
| 2006/0132283 A1 | 6/2006 | Eberhart et al. |
| 2006/0144440 A1 | 7/2006 | Merkle |
| 2006/0149171 A1 | 7/2006 | Vogel et al. |
| 2006/0155584 A1 | 7/2006 | Aggarwal |
| 2006/0190130 A1 | 8/2006 | Fedor et al. |
| 2006/0224051 A1 | 10/2006 | Teller et al. |
| 2006/0229557 A1 | 10/2006 | Fathallah et al. |
| 2006/0246922 A1 | 11/2006 | Gasbarro et al. |
| 2006/0255935 A1 | 11/2006 | Scalisi et al. |
| 2007/0005029 A1 | 1/2007 | Hopkins et al. |
| 2007/0016152 A1 | 1/2007 | Karpowicz et al. |
| 2007/0032741 A1 | 2/2007 | Hibner et al. |
| 2007/0032762 A1 | 2/2007 | Vogel |
| 2007/0032763 A1 | 2/2007 | Vogel |
| 2007/0052683 A1 | 3/2007 | Knott et al. |
| 2007/0055209 A1 | 3/2007 | Patel et al. |
| 2007/0078444 A1 | 4/2007 | Larsson |
| 2007/0118096 A1 | 5/2007 | Smith et al. |
| 2007/0138069 A1 | 6/2007 | Roncadi et al. |
| 2007/0167927 A1 | 7/2007 | Hunt et al. |
| 2007/0179460 A1 | 8/2007 | Adahan |
| 2007/0180904 A1 | 8/2007 | Gao |
| 2007/0219480 A1 | 9/2007 | Kamen et al. |
| 2007/0227360 A1 | 10/2007 | Atlas et al. |
| 2007/0227537 A1 | 10/2007 | Bemister et al. |
| 2007/0233022 A1 | 10/2007 | Henley et al. |
| 2007/0250009 A1 | 10/2007 | Barak |
| 2007/0255114 A1 | 11/2007 | Ackermann et al. |
| 2007/0255116 A1 | 11/2007 | Mehta et al. |
| 2007/0260226 A1 | 11/2007 | Jaeb et al. |
| 2007/0271298 A1 | 11/2007 | Juang et al. |
| 2007/0276309 A1 | 11/2007 | Xu et al. |
| 2007/0282249 A1 | 12/2007 | Quisenberry et al. |
| 2008/0004818 A1 | 1/2008 | Zaleski |
| 2008/0005000 A1 | 1/2008 | Radl et al. |
| 2008/0009681 A1 | 1/2008 | Al Hussiny |
| 2008/0015526 A1 | 1/2008 | Reiner et al. |
| 2008/0039761 A1 | 2/2008 | Heaton et al. |
| 2008/0041401 A1 | 2/2008 | Casola et al. |
| 2008/0051708 A1 | 2/2008 | Kumar et al. |
| 2008/0071209 A1 | 3/2008 | Moubayed et al. |
| 2008/0071216 A1 | 3/2008 | Locke et al. |
| 2008/0071234 A1 | 3/2008 | Kelch et al. |
| 2008/0071235 A1 | 3/2008 | Locke et al. |
| 2008/0077091 A1 | 3/2008 | Mulligan |
| 2008/0082040 A1 | 4/2008 | Kubler et al. |
| 2008/0082077 A1 | 4/2008 | Williams |
| 2008/0086357 A1 | 4/2008 | Choubey et al. |
| 2008/0091175 A1 | 4/2008 | Frikart et al. |
| 2008/0091659 A1 | 4/2008 | McFaul |
| 2008/0112461 A1 | 5/2008 | Bisch et al. |
| 2008/0125697 A1 | 5/2008 | Gao |
| 2008/0125698 A1 | 5/2008 | Gerg et al. |
| 2008/0126126 A1 | 5/2008 | Ballai |
| 2008/0140160 A1 | 6/2008 | Goetz et al. |
| 2008/0167534 A1 | 7/2008 | Young et al. |
| 2008/0177224 A1 | 7/2008 | Kelly et al. |
| 2008/0180268 A1 | 7/2008 | Nissels et al. |
| 2008/0200868 A1 | 8/2008 | Alberti et al. |
| 2008/0200905 A1 | 8/2008 | Heaton et al. |
| 2008/0200906 A1 | 8/2008 | Sanders et al. |
| 2008/0208147 A1 | 8/2008 | Argenta et al. |
| 2008/0209357 A1 | 8/2008 | Vasta et al. |
| 2008/0221396 A1 | 9/2008 | Garces et al. |
| 2008/0228526 A1 | 9/2008 | Locke et al. |
| 2008/0234641 A1 | 9/2008 | Locke et al. |
| 2008/0242945 A1 | 10/2008 | Gugliotti et al. |
| 2008/0243096 A1 | 10/2008 | Svedman |
| 2008/0249377 A1 | 10/2008 | Molducci et al. |
| 2008/0272254 A1 | 11/2008 | Harr et al. |

(56) References Cited

U.S. PATENT DOCUMENTS

| | | |
|---|---|---|
| 2008/0281281 A1 | 11/2008 | Meyer et al. |
| 2008/0300572 A1 | 12/2008 | Rankers et al. |
| 2008/0307353 A1 | 12/2008 | Molducci et al. |
| 2009/0005746 A1 | 1/2009 | Nielsen et al. |
| 2009/0037216 A1 | 2/2009 | Bluemler et al. |
| 2009/0037220 A1 | 2/2009 | Chambers et al. |
| 2009/0043268 A1 | 2/2009 | Eddy et al. |
| 2009/0048492 A1 | 2/2009 | Rantala et al. |
| 2009/0048865 A1 | 2/2009 | Breazeale, Jr. |
| 2009/0082741 A1 | 3/2009 | Hu |
| 2009/0099866 A1 | 4/2009 | Newman |
| 2009/0099867 A1 | 4/2009 | Newman |
| 2009/0101219 A1 | 4/2009 | Martini et al. |
| 2009/0115663 A1 | 5/2009 | Brown et al. |
| 2009/0118591 A1 | 5/2009 | Kim et al. |
| 2009/0125055 A1 | 5/2009 | Larkin et al. |
| 2009/0125331 A1 | 5/2009 | Pamsgaard et al. |
| 2009/0144091 A1 | 6/2009 | Rago |
| 2009/0171166 A1 | 7/2009 | Amundson et al. |
| 2009/0171288 A1 | 7/2009 | Wheeler |
| 2009/0171289 A1 | 7/2009 | Davis et al. |
| 2009/0182266 A1 | 7/2009 | Gordon et al. |
| 2009/0182594 A1 | 7/2009 | Choubey |
| 2009/0187424 A1 | 7/2009 | Grabowski |
| 2009/0204434 A1 | 8/2009 | Breazeale, Jr. |
| 2009/0204435 A1 | 8/2009 | Gale |
| 2009/0206017 A1 | 8/2009 | Rohde et al. |
| 2009/0254362 A1 | 10/2009 | Choubey et al. |
| 2009/0270833 A1 | 10/2009 | DeBelser et al. |
| 2009/0281867 A1 | 11/2009 | Sievenpiper et al. |
| 2009/0292264 A1 | 11/2009 | Hudspeth et al. |
| 2009/0299306 A1 | 12/2009 | Buan |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0010646 A1 | 1/2010 | Drew et al. |
| 2010/0020021 A1 | 1/2010 | Mills et al. |
| 2010/0022990 A1 | 1/2010 | Karpowicz et al. |
| 2010/0036333 A1 | 2/2010 | Schenk, III et al. |
| 2010/0042021 A1 | 2/2010 | Hu et al. |
| 2010/0042059 A1 | 2/2010 | Pratt et al. |
| 2010/0056875 A1 | 3/2010 | Schoenberg et al. |
| 2010/0063483 A1 | 3/2010 | Adahan |
| 2010/0069829 A1 | 3/2010 | Hutchinson et al. |
| 2010/0090004 A1 | 4/2010 | Sands et al. |
| 2010/0114026 A1 | 5/2010 | Karratt et al. |
| 2010/0121257 A1 | 5/2010 | King |
| 2010/0126268 A1 | 5/2010 | Baily et al. |
| 2010/0137775 A1 | 6/2010 | Hu et al. |
| 2010/0145161 A1 | 6/2010 | Niyato et al. |
| 2010/0145289 A1 | 6/2010 | Lina et al. |
| 2010/0150991 A1 | 6/2010 | Bernstein |
| 2010/0168687 A1 | 7/2010 | Yu |
| 2010/0191178 A1 | 7/2010 | Ross et al. |
| 2010/0191199 A1 | 7/2010 | Evans et al. |
| 2010/0200486 A1 | 8/2010 | Guenther et al. |
| 2010/0204663 A1 | 8/2010 | Wudyka |
| 2010/0211030 A1 | 8/2010 | Turner et al. |
| 2010/0222645 A1 | 9/2010 | Nadler et al. |
| 2010/0228205 A1 | 9/2010 | Hu et al. |
| 2010/0234708 A1 | 9/2010 | Buck et al. |
| 2010/0251114 A1 | 9/2010 | Wehba et al. |
| 2010/0255876 A1 | 10/2010 | Jordan et al. |
| 2010/0268179 A1 | 10/2010 | Kelch et al. |
| 2010/0274177 A1 | 10/2010 | Rybski et al. |
| 2010/0280435 A1 | 11/2010 | Raney et al. |
| 2010/0280536 A1 | 11/2010 | Hartwell |
| 2010/0282834 A1 | 11/2010 | Devergne et al. |
| 2010/0305490 A1 | 12/2010 | Coulthard et al. |
| 2010/0305523 A1 | 12/2010 | Vess |
| 2010/0313958 A1 | 12/2010 | Patel et al. |
| 2010/0314517 A1 | 12/2010 | Patzer |
| 2010/0317933 A1 | 12/2010 | Colman et al. |
| 2010/0318043 A1 | 12/2010 | Malhi et al. |
| 2010/0318071 A1 | 12/2010 | Wudyka |
| 2011/0003610 A1 | 1/2011 | Key et al. |
| 2011/0004188 A1 | 1/2011 | Shekalim |
| 2011/0006876 A1 | 1/2011 | Moberg et al. |
| 2011/0009824 A1 | 1/2011 | Yodfat et al. |
| 2011/0015585 A1 | 1/2011 | Svedman et al. |
| 2011/0015587 A1 | 1/2011 | Tumey et al. |
| 2011/0015590 A1 | 1/2011 | Svedman et al. |
| 2011/0028881 A1 | 2/2011 | Basaglia |
| 2011/0028882 A1 | 2/2011 | Basaglia |
| 2011/0028921 A1 | 2/2011 | Hartwell et al. |
| 2011/0034861 A1 | 2/2011 | Schaefer |
| 2011/0038741 A1 | 2/2011 | Lissner et al. |
| 2011/0040268 A1 | 2/2011 | Eckstein et al. |
| 2011/0040288 A1 | 2/2011 | Eckstein et al. |
| 2011/0054810 A1 | 3/2011 | Turner et al. |
| 2011/0063117 A1 | 3/2011 | Turner et al. |
| 2011/0066096 A1 | 3/2011 | Svedman |
| 2011/0066110 A1 | 3/2011 | Fathallah et al. |
| 2011/0066123 A1 | 3/2011 | Tout et al. |
| 2011/0071415 A1 | 3/2011 | Karwoski et al. |
| 2011/0071844 A1 | 3/2011 | Cannon et al. |
| 2011/0077605 A1 | 3/2011 | Karpowicz et al. |
| 2011/0092927 A1 | 4/2011 | Wilkes et al. |
| 2011/0092958 A1 | 4/2011 | Jacobs |
| 2011/0106028 A1 | 5/2011 | Giezendanner et al. |
| 2011/0106561 A1 | 5/2011 | Eaton, Jr. et al. |
| 2011/0107251 A1 | 5/2011 | Guaitoli et al. |
| 2011/0112492 A1 | 5/2011 | Bharti et al. |
| 2011/0112857 A1 | 5/2011 | Yurko et al. |
| 2011/0130712 A1 | 6/2011 | Topaz |
| 2011/0137759 A1 | 6/2011 | Wellington et al. |
| 2011/0152739 A1 | 6/2011 | Roncadi et al. |
| 2011/0173028 A1 | 7/2011 | Bond |
| 2011/0190703 A1 | 8/2011 | Pratt et al. |
| 2011/0196321 A1 | 8/2011 | Wudyka |
| 2011/0230849 A1 | 9/2011 | Coulthard et al. |
| 2011/0245682 A1 | 10/2011 | Robinson et al. |
| 2011/0246219 A1 | 10/2011 | Smith et al. |
| 2011/0251569 A1 | 10/2011 | Turner et al. |
| 2011/0257572 A1 | 10/2011 | Locke et al. |
| 2011/0288511 A1 | 11/2011 | Locke et al. |
| 2011/0290979 A1 | 12/2011 | Henault et al. |
| 2011/0313789 A1 | 12/2011 | Kamen et al. |
| 2011/0315611 A1 | 12/2011 | Fulkerson et al. |
| 2011/0319813 A1 | 12/2011 | Kamen et al. |
| 2012/0001762 A1 | 1/2012 | Turner et al. |
| 2012/0032819 A1 | 2/2012 | Chae et al. |
| 2012/0035427 A1 | 2/2012 | Friedman et al. |
| 2012/0035560 A1 | 2/2012 | Eddy et al. |
| 2012/0035561 A1 | 2/2012 | Locke et al. |
| 2012/0046624 A1 | 2/2012 | Locke et al. |
| 2012/0046625 A1 | 2/2012 | Johannison |
| 2012/0071845 A1 | 3/2012 | Hu et al. |
| 2012/0078539 A1 | 3/2012 | Vernon-Harcourt et al. |
| 2012/0081225 A1 | 4/2012 | Waugh et al. |
| 2012/0123323 A1 | 5/2012 | Kagan et al. |
| 2012/0123358 A1 | 5/2012 | Hall et al. |
| 2012/0157889 A1 | 6/2012 | Tanis et al. |
| 2012/0157941 A1 | 6/2012 | Luckemeyer et al. |
| 2012/0176394 A1 | 7/2012 | Vik et al. |
| 2012/0181405 A1 | 7/2012 | Zlatic et al. |
| 2012/0182143 A1 | 7/2012 | Gaines et al. |
| 2012/0184930 A1 | 7/2012 | Johannison |
| 2012/0184932 A1 | 7/2012 | Giezendanner et al. |
| 2012/0197196 A1 | 8/2012 | Halbert et al. |
| 2012/0197580 A1 | 8/2012 | Vij et al. |
| 2012/0209228 A1 | 8/2012 | Croizat et al. |
| 2012/0212434 A1 | 8/2012 | Bluemler et al. |
| 2012/0212455 A1 | 8/2012 | Kloeffel |
| 2012/0215455 A1 | 8/2012 | Patil et al. |
| 2012/0220960 A1 | 8/2012 | Ruland |
| 2012/0226247 A1 | 9/2012 | Danei et al. |
| 2012/0226768 A1 | 9/2012 | Gaines et al. |
| 2012/0259283 A1 | 10/2012 | Haase |
| 2012/0259651 A1 | 10/2012 | Mallon et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0289914 A1 | 11/2012 | Eckstein et al. |

(56) References Cited

U.S. PATENT DOCUMENTS

| | | |
|---|---|---|
| 2012/0290217 A1 | 11/2012 | Shoval et al. |
| 2012/0293322 A1 | 11/2012 | Ray et al. |
| 2012/0295566 A1 | 11/2012 | Collins et al. |
| 2012/0302976 A1 | 11/2012 | Locke et al. |
| 2012/0310205 A1 | 12/2012 | Lee et al. |
| 2013/0018355 A1 | 1/2013 | Brand et al. |
| 2013/0019744 A1 | 1/2013 | Hu |
| 2013/0023719 A1 | 1/2013 | Bennett |
| 2013/0028788 A1 | 1/2013 | Gronau et al. |
| 2013/0030394 A1 | 1/2013 | Locke et al. |
| 2013/0035615 A1 | 2/2013 | Hsieh |
| 2013/0053692 A1 | 2/2013 | Barron et al. |
| 2013/0060152 A1 | 3/2013 | Baron |
| 2013/0062265 A1 | 3/2013 | Balschat et al. |
| 2013/0066285 A1 | 3/2013 | Locke et al. |
| 2013/0066301 A1 | 3/2013 | Locke et al. |
| 2013/0073303 A1 | 3/2013 | Hsu |
| 2013/0076528 A1 | 3/2013 | Boettner et al. |
| 2013/0088452 A1 | 4/2013 | Glaser-Seidnitzer et al. |
| 2013/0090613 A1 | 4/2013 | Kelch et al. |
| 2013/0090949 A1 | 4/2013 | Tibebu |
| 2013/0102836 A1 | 4/2013 | Millman |
| 2013/0103419 A1 | 4/2013 | Beaudry |
| 2013/0123755 A1 | 5/2013 | Locke et al. |
| 2013/0124227 A1 | 5/2013 | Ellis |
| 2013/0133036 A1 | 5/2013 | Wang et al. |
| 2013/0144227 A1 | 6/2013 | Locke et al. |
| 2013/0144230 A1 | 6/2013 | Wu et al. |
| 2013/0150686 A1 | 6/2013 | Fronterhouse et al. |
| 2013/0150813 A1 | 6/2013 | Gordon et al. |
| 2013/0159456 A1 | 6/2013 | Daoud et al. |
| 2013/0160767 A1 | 6/2013 | Abella |
| 2013/0165821 A1 | 6/2013 | Freedman et al. |
| 2013/0165854 A1 | 6/2013 | Sandhu et al. |
| 2013/0165877 A1 | 6/2013 | Leeson et al. |
| 2013/0169432 A1 | 7/2013 | Ozgul et al. |
| 2013/0176230 A1 | 7/2013 | Georgiev et al. |
| 2013/0186405 A1 | 7/2013 | Krzyzanowski et al. |
| 2013/0190717 A1 | 7/2013 | Dollar et al. |
| 2013/0190903 A1 | 7/2013 | Balakrishnan et al. |
| 2013/0196703 A1 | 8/2013 | Masoud et al. |
| 2013/0198685 A1 | 8/2013 | Bernini et al. |
| 2013/0204210 A1 | 8/2013 | Pratt et al. |
| 2013/0212168 A1 | 8/2013 | Bonasera et al. |
| 2013/0214925 A1 | 8/2013 | Weiss |
| 2013/0223979 A1 | 8/2013 | Locke et al. |
| 2013/0226607 A1 | 8/2013 | Woody et al. |
| 2013/0231596 A1 | 9/2013 | Hornbach et al. |
| 2013/0245387 A1 | 9/2013 | Patel |
| 2013/0245580 A1 | 9/2013 | Locke et al. |
| 2013/0253952 A1 | 9/2013 | Burke et al. |
| 2013/0254717 A1 | 9/2013 | Al-Ali et al. |
| 2013/0262730 A1 | 10/2013 | Al-Ali et al. |
| 2013/0267917 A1 | 10/2013 | Pan et al. |
| 2013/0267918 A1 | 10/2013 | Pan et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0275145 A1 | 10/2013 | Moore et al. |
| 2013/0285837 A1 | 10/2013 | Uchida |
| 2013/0289536 A1 | 10/2013 | Croizat et al. |
| 2013/0293570 A1 | 11/2013 | Dolgos et al. |
| 2013/0297350 A1 | 11/2013 | Gross et al. |
| 2013/0303975 A1 | 11/2013 | Gvodas, Jr. |
| 2013/0310631 A1 | 11/2013 | Lee et al. |
| 2013/0310726 A1 | 11/2013 | Miller et al. |
| 2013/0310778 A1 | 11/2013 | Locke et al. |
| 2013/0317420 A1 | 11/2013 | Wehmeyer |
| 2013/0317463 A1 | 11/2013 | Yao et al. |
| 2013/0325508 A1 | 12/2013 | Johnson et al. |
| 2013/0327326 A1 | 12/2013 | Brennan |
| 2013/0331822 A1 | 12/2013 | Patel et al. |
| 2013/0332197 A1 | 12/2013 | Hinkel |
| 2013/0335233 A1 | 12/2013 | Kamar et al. |
| 2013/0345524 A1 | 12/2013 | Meyer et al. |
| 2014/0018727 A1 | 1/2014 | Burbank et al. |
| 2014/0031884 A1 | 1/2014 | Elghazzawi |
| 2014/0032231 A1 | 1/2014 | Semen et al. |
| 2014/0052202 A1 | 2/2014 | Daynes |
| 2014/0055588 A1 | 2/2014 | Bangera et al. |
| 2014/0058344 A1 | 2/2014 | Toth |
| 2014/0100516 A1 | 4/2014 | Hunt et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0114236 A1 | 4/2014 | Gordon |
| 2014/0114237 A1 | 4/2014 | Gordon |
| 2014/0129250 A1 | 5/2014 | Daniel et al. |
| 2014/0136218 A1 | 5/2014 | Bolene et al. |
| 2014/0148138 A1 | 5/2014 | Chou |
| 2014/0163490 A1 | 6/2014 | Locke et al. |
| 2014/0163493 A1 | 6/2014 | Weston et al. |
| 2014/0194835 A1 | 7/2014 | Ehlert |
| 2014/0236106 A1 | 8/2014 | Locke et al. |
| 2014/0303551 A1 | 10/2014 | Germain et al. |
| 2014/0323906 A1 | 10/2014 | Peatfield et al. |
| 2015/0025482 A1 | 1/2015 | Begin et al. |
| 2015/0025485 A1 | 1/2015 | Luckemeyer et al. |
| 2015/0025486 A1 | 1/2015 | Hu et al. |
| 2015/0051560 A1 | 2/2015 | Askem |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0133829 A1 | 5/2015 | DeBusk et al. |
| 2015/0159066 A1 | 6/2015 | Hartwell et al. |
| 2015/0174304 A1 | 6/2015 | Askem et al. |
| 2016/0184496 A1 | 6/2016 | Jaecklein et al. |

FOREIGN PATENT DOCUMENTS

| | | |
|---|---|---|
| DE | 102010036405 A1 | 1/2012 |
| DE | 202014101752 U1 | 6/2014 |
| EP | 0829228 A1 | 3/1998 |
| EP | 0904788 B1 | 11/2003 |
| EP | 1684146 A2 | 7/2006 |
| EP | 1702649 A1 | 9/2006 |
| EP | 1788503 A2 | 5/2007 |
| EP | 1797918 A1 | 6/2007 |
| EP | 1857950 A2 | 11/2007 |
| EP | 2172859 A1 | 4/2010 |
| EP | 2218478 A1 | 8/2010 |
| EP | 2246079 A1 | 11/2010 |
| EP | 2248545 A1 | 11/2010 |
| EP | 1668556 B1 | 2/2011 |
| EP | 2366721 A1 | 9/2011 |
| EP | 1248660 B1 | 4/2012 |
| EP | 1248661 B1 | 8/2012 |
| EP | 2503478 A2 | 9/2012 |
| EP | 2505169 A3 | 12/2012 |
| EP | 2529765 A2 | 12/2012 |
| EP | 2562665 A2 | 2/2013 |
| EP | 2389961 B1 | 3/2013 |
| EP | 2674845 A1 | 12/2013 |
| EP | 2650027 A3 | 1/2014 |
| EP | 1565219 B1 | 2/2014 |
| EP | 2066365 B1 | 4/2015 |
| GB | 2235877 A | 3/1991 |
| GB | 2279784 A | 1/1995 |
| GB | 2342584 A | 4/2000 |
| GB | 2409951 A | 7/2005 |
| GB | 2475091 A | 5/2011 |
| GB | 2488904 A | 9/2012 |
| WO | WO-9619335 A1 | 6/1996 |
| WO | WO-0114048 A1 | 3/2001 |
| WO | WO-0136027 A1 | 5/2001 |
| WO | WO-03055432 A1 | 7/2003 |
| WO | WO-03094090 A2 | 11/2003 |
| WO | WO-03101508 A2 | 12/2003 |
| WO | WO-2005109297 A2 | 11/2005 |
| WO | WO-2008036344 A1 | 3/2008 |
| WO | WO-2008036360 A2 | 3/2008 |
| WO | WO-2008039314 A2 | 4/2008 |
| WO | WO-2008100440 A1 | 8/2008 |
| WO | WO-2008104609 A1 | 9/2008 |

(56) References Cited

FOREIGN PATENT DOCUMENTS

| | | |
|---|---|---|
| WO | WO-2008116295 A1 | 10/2008 |
| WO | WO-2008132215 A1 | 11/2008 |
| WO | WO-2009021523 A1 | 2/2009 |
| WO | WO-2009047524 A2 | 4/2009 |
| WO | WO-2009089390 A2 | 7/2009 |
| WO | WO-2009093116 A1 | 7/2009 |
| WO | WO-2009151645 A2 | 12/2009 |
| WO | WO-2010017484 A2 | 2/2010 |
| WO | WO-2010039481 A1 | 4/2010 |
| WO | WO-2010085033 A2 | 7/2010 |
| WO | WO-2010089368 A2 | 8/2010 |
| WO | WO-2010126668 A1 | 11/2010 |
| WO | WO-2010145780 A1 | 12/2010 |
| WO | WO-2011023275 A1 | 3/2011 |
| WO | WO-2011107972 A1 | 9/2011 |
| WO | WO-2011124388 A1 | 10/2011 |
| WO | WO-2011137230 A1 | 11/2011 |
| WO | WO-2012009869 A1 | 1/2012 |
| WO | WO-2012027342 A1 | 3/2012 |
| WO | WO-2012027912 A1 | 3/2012 |
| WO | WO-2012027913 A1 | 3/2012 |
| WO | WO-2012027914 A1 | 3/2012 |
| WO | WO-2012027915 A1 | 3/2012 |
| WO | WO-2012027916 A1 | 3/2012 |
| WO | WO-2012051278 A1 | 4/2012 |
| WO | WO-2012100624 A1 | 8/2012 |
| WO | WO-2012107430 A1 | 8/2012 |
| WO | WO-2012127281 A1 | 9/2012 |
| WO | WO-2012156655 A1 | 11/2012 |
| WO | WO-2012160164 A1 | 11/2012 |
| WO | WO-2012172818 A1 | 12/2012 |
| WO | WO-2013014278 A1 | 1/2013 |
| WO | WO-2013025815 A1 | 2/2013 |
| WO | WO-2013029330 A1 | 3/2013 |
| WO | WO-2013054217 A1 | 4/2013 |
| WO | WO-2013063848 A1 | 5/2013 |
| WO | WO-2013066775 A1 | 5/2013 |
| WO | WO-2013078214 A1 | 5/2013 |
| WO | WO-2013089712 A1 | 6/2013 |
| WO | WO-2013102855 A1 | 7/2013 |
| WO | WO-2013109517 A1 | 7/2013 |
| WO | WO-2013119978 A1 | 8/2013 |
| WO | WO-2013123022 A1 | 8/2013 |
| WO | WO-2013126049 A1 | 8/2013 |
| WO | WO-2013141870 A1 | 9/2013 |
| WO | WO-2013150025 A1 | 10/2013 |
| WO | WO-2013175076 A1 | 11/2013 |
| WO | WO-2013182218 A1 | 12/2013 |
| WO | WO-2014012802 A1 | 1/2014 |
| WO | WO-2014151930 A2 | 9/2014 |
| WO | WO-2014009876 A3 | 12/2014 |
| WO | WO-2015023515 A1 | 2/2015 |
| WO | WO-2015091070 A1 | 6/2015 |
| WO | WO-2015197462 A1 | 12/2015 |
| WO | WO-2016018448 A1 | 2/2016 |

OTHER PUBLICATIONS

Hartmann Vivano., "Vivano—Product Application Description," retrieved from http://www.vivanosystem.info/20809.php, accessed on Feb. 28, 2013, 3 pages.
Huntleigh Healthcare, "Negative Pressure Positive Outcomes," WoundASSIST TNP Console and Canister Brochure, 2007, 6 pages.
International Preliminary Report on Patentability for Application No. PCT/US2014/026692, mailed on Sep. 24, 2015, 16 pages.
International Preliminary Report on Patentability for Application No. PCT/US2014/050233, mailed on Feb. 16, 2016, 10 pages.
International Search Report and Written Opinion for Application No. PCT/GB2014/050786, mailed on Jun. 12, 2014, 14 pages.
International Search Report and Written Opinion for Application No. PCT/US2014/026692, mailed on Mar. 2, 2015, 26 pages.
International Search Report and Written Opinion for Application No. PCT/US2014/050233, mailed on Jan. 7, 2015, 16 pages.
International Search Report and Written Opinion for Application No. PCT/US2014/066441, mailed on Jun. 25, 2015, 16 pages.
Invitation to Pay and Partial International Search Report for Application No. PCT/US2014/026692, mailed on Sep. 26, 2014, 9 pages.
Invitation to Pay and Partial International Search Report for Application No. PCT/US2014/050233, mailed on Nov. 5, 2014, 8 pages.

BLOCKAGE AND CANISTER FULL DETECTION IN REDUCED PRESSURE THERAPY SYSTEMS

CROSS-REFERENCE TO RELATED APPLICATIONS

This application is a continuation of U.S. application Ser. No. 16/219,641, filed Dec. 13, 2018, which is a continuation of U.S. application Ser. No. 14/912,071, filed Feb. 12, 2016, which is a national stage application of International Patent Application No. PCT/US2014/050233, filed Aug. 7, 2014, which claims the benefit of U.S. Provisional Application No. 61/865,516, filed on Aug. 13, 2013, the disclosures of which are hereby incorporated by reference in their entireties.

BACKGROUND

Field

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP systems.

Description of the Related Art

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and method of using TNP systems. In addition, embodiments disclosed herein relate to attachment mechanisms or systems for negative pressure therapy devices.

SUMMARY

In some embodiments, a negative pressure wound therapy apparatus includes a negative pressure source configured to be in fluid communication with a wound dressing, the negative pressure source configured to provide negative pressure to the wound, a canister configured to be in fluid communication with the dressing and the negative pressure source, the canister configured to collect exudate removed from the wound, and a pressure sensor configured to monitor one or more characteristics of pressure signals generated by the negative pressure source. The apparatus also includes a controller configured to determine a level of exudate in the canister based at least in part on the measured one or more characteristics of the pressure signals.

The apparatus of the preceding paragraph may also include any combination of the following features described in this paragraph, among others described herein. The measured one or more characteristics of the pressure signals can include magnitude of the pressure signals, and the magnitude of the pressure signals can increase as the level of exudate in the canister increases. The canister can include a filter configured to become occluded in order to prevent overflow of the canister and the controller can be further configured to detect a canister pre-full condition before the filter becomes occluded. The controller can also provide an indication of the canister pre-full condition to a user. The controller can be configured to determine the level of exudate in the canister based at least in part on the measured one or more characteristics of the pressure signals and a measured activity level of the negative pressure source. The negative pressure source can include a vacuum pump and the activity level of the negative pressure source corresponds to a speed of the vacuum pump. The apparatus can include a tachometer configured to measure the speed of the vacuum pump.

The apparatus of any of the preceding paragraphs may also include any combination of the following features described in this paragraph, among others described herein. The apparatus can include a fluid flow path configured to fluidically connect the dressing, the canister, and the negative pressure source, and the controller can be further configured to determine a leak rate of fluid in the flow path based at least in part on the activity level of the negative pressure source and determine the level of exudate in the canister based at least in part on the measured one or more characteristics of the pressure signals and the determined leak rate. The controller can be configured to remove noise from the measured one or more characteristics of the pressure signals. The controller can be configured to determine the level of exudate in the canister based at least in part on comparing the measured one or more characteristics of the pressure signals to one or more thresholds. The measured one or more characteristics can include magnitude and frequency of pressure pulses and the controller can be configured to determine the level of exudate in the canister based at least in part on the magnitude and frequency of the pressure signals. The magnitude of the pressure signals can increase as the level of exudate in the canister increases and the frequency of the pressure signals can decrease as the level of exudate in the canister increases.

The apparatus of any of the preceding paragraphs may also include any combination of the following features described in this paragraph, among others described herein. The controller can be configured to determine the level of exudate in the canister irrespective of an intensity of a leak present in a fluid flow path configured to fluidically connect the dressing, the canister, and the negative pressure source. The controller can be configured to determine the level of exudate in the canister based at least in part on a change in the measured one or more characteristics of the pressure signals. The apparatus can include a wound dressing configured to be placed over a wound.

In certain embodiments, a method of operating a negative pressure wound therapy apparatus includes monitoring pressure signals generated by a negative pressure source in fluid communication with a wound dressing and a canister and determining a level of aspirated exudate in the canister based at least in part on one or more characteristics of the monitored pressure signals.

The method of the preceding paragraph may also include any combination of the following features described in this paragraph, among others described herein. One or more characteristics of the monitored pressure signals can include magnitude of the pressure signals, and the magnitude of the pressure signals can increase as the level of exudate in the canister increases. The canister can include a filter configured to become occluded in order to prevent overflow of the canister and the method can further include detecting a canister pre-full condition before the filter becomes occluded. An indication of the canister pre-full condition can be provided to a user. The method can include measuring activity level of the negative pressure source and determining the level of exudate in the canister based at least in part on the one or more characteristics of the monitored pressure signals and the measured activity level. The negative pressure source can include a vacuum pump and the activity level of the negative pressure source corresponds to a speed of the vacuum pump. A tachometer can used to measure the speed of the vacuum pump. The method can include determining a leak rate of fluid in a flow path based at least in part on the activity level of the negative pressure source and determining the level of exudate in the canister based at least in part on the one or more characteristics of the monitored pressure signals and the determined leak rate. The fluid flow path can fluidically connect a dressing placed over a wound, the negative pressure source, and the canister.

The method of any of the preceding paragraphs may also include any combination of the following features described in this paragraph, among others described herein. The method can include removing noise from the pressure signal measurements. The method can include determining the level of exudate in the canister based at least in part on comparing the one or more characteristics of the monitored pressure signals to one or more thresholds. The one or more characteristics of the monitored pressure signals can include magnitude and frequency of the pressure signals and the method can further include determining the level of exudate in the canister based at least in part on the magnitude and the frequency of the monitored pressure signals. The magnitude of the pressure signals can increase as the level of exudate in the canister increases and the frequency of the pressure signals can decrease as the level of exudate in the canister increases. Determining the level of aspirated exudate in the canister is performed irrespective of an intensity of a leak present in a fluid flow fluidically connecting the dressing, the canister, and the negative pressure source. The method can include determining the level of exudate in the canister based at least in part on a change in the one or more characteristics of the monitored pressure signals.

In various embodiments, a negative pressure wound therapy apparatus includes a dressing configured to be placed over a wound, the dressing configured to collect exudate removed from the wound, a negative pressure source configured to be in fluid communication with the dressing, the negative pressure source configured to provide negative pressure to the wound, and a pressure sensor configured to monitor one or more characteristics of pressure signals generated by the negative pressure source. The apparatus also includes a controller configured to determine a level of exudate in the dressing based at least in part on the monitored one or more characteristics of the pressure signals.

The apparatus of any of the preceding paragraphs may also include any combination of the following features described in this paragraph, among others described herein. The monitored one or more characteristics of the pressure signals can include magnitude of the pressure signals, and the magnitude of the pressure signals can increase as the level of exudate in the dressing increases. The dressing can include a filter configured to become occluded in order to prevent overflow and the controller can be further configured to detect a dressing pre-full condition before the filter becomes occluded and provide an indication of the dressing pre-full condition to a user. The controller can be further configured to determine the level of exudate in the dressing based at least in part on the monitored one or more characteristics of the pressure signals and a measured activity level of the negative pressure source. The apparatus can further include a fluid flow path configured to fludically connect the dressing and the negative pressure source and the controller can be further configured to determine a leak rate of fluid in the flow path based at least in part on the activity level of the negative pressure source and to determine the level of exudate in the dressing based at least in part on the monitored one or more characteristics of the pressure signals and the determined leak rate.

The apparatus of any of the preceding paragraphs may also include any combination of the following features described in this paragraph, among others described herein. The controller can be configured to determine the level of exudate in the dressing based at least in part on comparing the monitored one or more characteristics of the pressure signals to one or more thresholds The monitored one or more characteristics of the pressure signals can include magnitude and frequency of the pressure signals and the controller can be further configured to determine the level of exudate in the dressing based at least in part on the magnitude and the frequency of the pressure signals. The magnitude of the pressure signals can increase as the level of exudate in the dressing increases and the frequency of the pressure signals can decrease as the level of exudate in the dressing increases. The controller can be configured to determine the level of exudate in the dressing irrespective of an intensity of a leak present in a fluid flow path configured to fluidically connect the dressing and negative pressure source. The controller can be configured to determine the level of exudate in the dressing based at least in part on a change in the monitored one or more characteristics of the pressure signals.

In some embodiments, a method of operating a negative wound therapy apparatus includes monitoring pressure signals generated by a negative pressure source in fluid communication with a wound dressing and a canister and determining a level of aspirated exudate in the dressing based at least in part on one or more characteristics of the monitored pressure signals.

The method of any of the preceding paragraphs may also include any combination of the following features described in this paragraph, among others described herein. The monitored one or more characteristics of the pressure signals include magnitude of the pressure signals, and wherein the magnitude of the pressure signals increases as the level of exudate in the dressing increases. The dressing can include a filter configured to become occluded in order to prevent overflow and the method can further include detecting a dressing pre-full condition before the filter becomes occluded and providing an indication of the dressing pre-full condition to a use. The method can further include measuring activity level of the negative pressure source and determining the level of exudate in the dressing based at least in part on the monitored one or more characteristics of the pressure signals and the measured activity level.

The method of any of the preceding paragraphs may also include any combination of the following features described in this paragraph, among others described herein. The method can include determining a leak rate of fluid in the flow path based at least in part on the activity level of the negative pressure source, the fluid flow path fludically connecting the dressing and the negative pressure source and determining the level of exudate in the dressing based at least in part on the monitored one or more characteristics of the pressure signals and the determined leak rate. The method can include determining the level of exudate in the dressing based at least in part on comparing the monitored one or more characteristics of the pressure signals to one or more thresholds. The monitored one or more characteristics of the pressure signals can include magnitude and frequency of the pressure signals and the method can further include determining the level of exudate in the dressing based at least in part on the magnitude and the frequency of the pressure signals. The magnitude of the pressure signals can increase as the level of exudate in the dressing increases and the frequency of the pressure signals can decrease as the level of exudate in the dressing increases. The method can further include determining the level of exudate in the dressing irrespective of an intensity of a leak present in a fluid flow path fluidically connecting the dressing and negative pressure source.

BRIEF DESCRIPTION OF THE DRAWINGS

Embodiments of the present invention will now be described hereinafter, by way of example only, with reference to the accompanying drawings in which.

DETAILED DESCRIPTION

Overview

Figure 1:
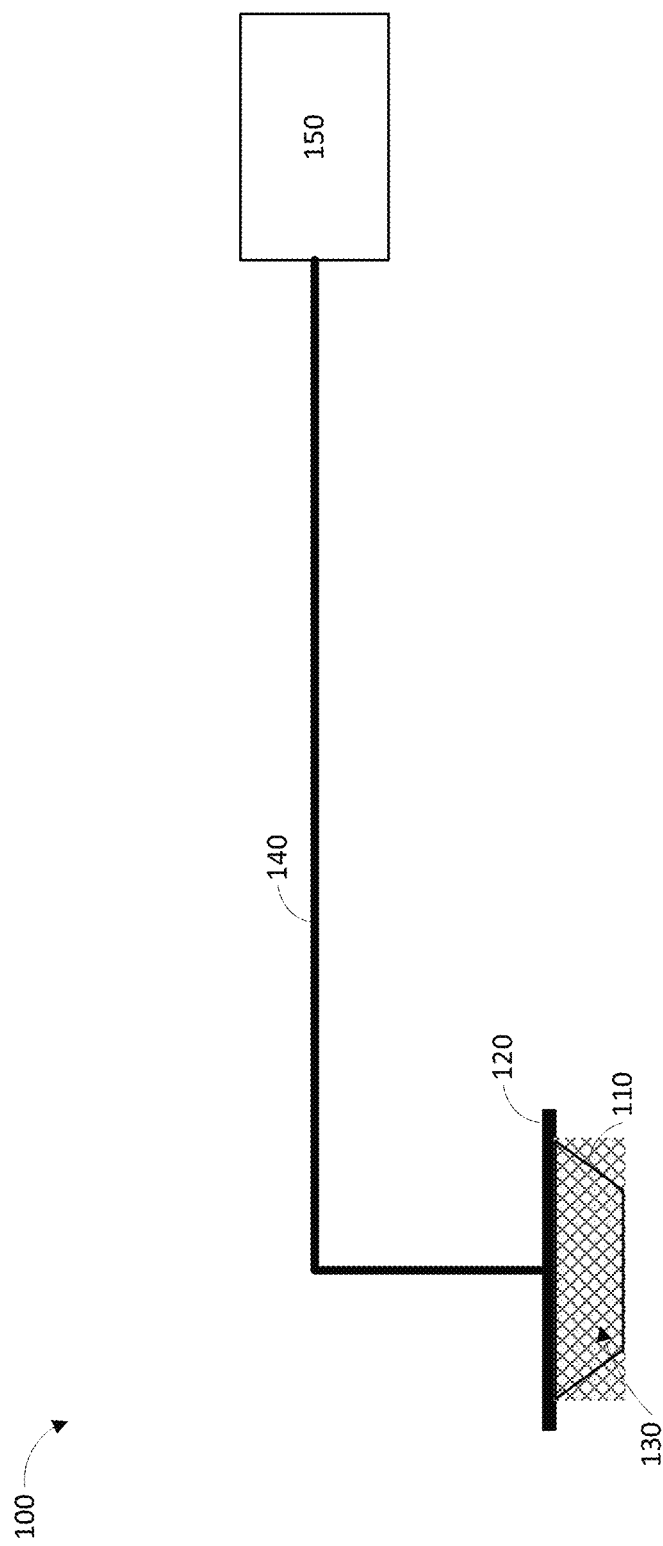
FIG. 1 illustrates a reduced pressure wound therapy system according to some embodiments.

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present invention are generally applicable to use in topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

In some embodiments, a negative pressure wound therapy apparatus includes a dressing configured to be placed over a wound and a source of negative pressure configured to be in fluid communication with the dressing. The source of negative pressure is configured to provide negative pressure to the wound. The apparatus can also include a canister configured to collect exudate removed from the wound. The canister can be configured to be in fluid communication with the dressing and the negative pressure source. The apparatus also includes a pressure sensor configured to monitor pressure signals generated by the negative pressure source and a controller. The controller can be configured to determine a level of exudate in the canister (or in the dressing) based at least in part on one or more characteristics of the monitored pressure signals. The one or more characteristics of the pressure signals can change as a level of exudate in the canister increases.

In various embodiments, a method of operating a negative pressure wound therapy apparatus includes monitoring pressure signals generated by a negative pressure source in fluid communication with a dressing and a canister. The method also includes determining a level of exudate in the canister (or in the dressing) based at least in part on one or more characteristics of the monitored pressure signals. The one or more characteristics of the pressure signals can change as a level of exudate in the canister increases.

In some embodiments, systems and methods for determining an amount of flow restriction or reduced volume in front of a negative pressure utilize one or more characteristics of monitored pressure signals. For example, the magnitude of the pressure signals can increase as restriction to flow increase, which effectively reduces the volume in front of a negative pressure source. The volume in front of the negative pressure source may decrease due to filling of a canister or dressing with exudate removed from a wound.

Negative Pressure System

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity at atmospheric pressure, and also may have a substantially reduced compressed volume when under negative pressure. The wound cover 120 can provide a substantially fluid impermeable seal over the wound cavity 110. In some embodiments, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material.

Some embodiments of the wound cover 120 can have a port (not shown) configured to receive an end of the conduit 140. In some embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. In some embodiments, though not required, the pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure at a desired negative pressure setpoint, which can be selected or programmed to be approximately −80 mmHg, or between about −20 mmHg and −200 mmHg (e.g., as selected by a user). Note that these pressures are relative to normal ambient atmospheric pressure thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points. Low set point can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high set points and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2012/0116334, 2011/0213287, 2011/0282309, 2012/0136325, 2013/0110058, which are incorporated by reference in their entireties. In other embodiments, other suitable wound dressings can be utilized.

Pump Assembly and Canister

Figure 2A:
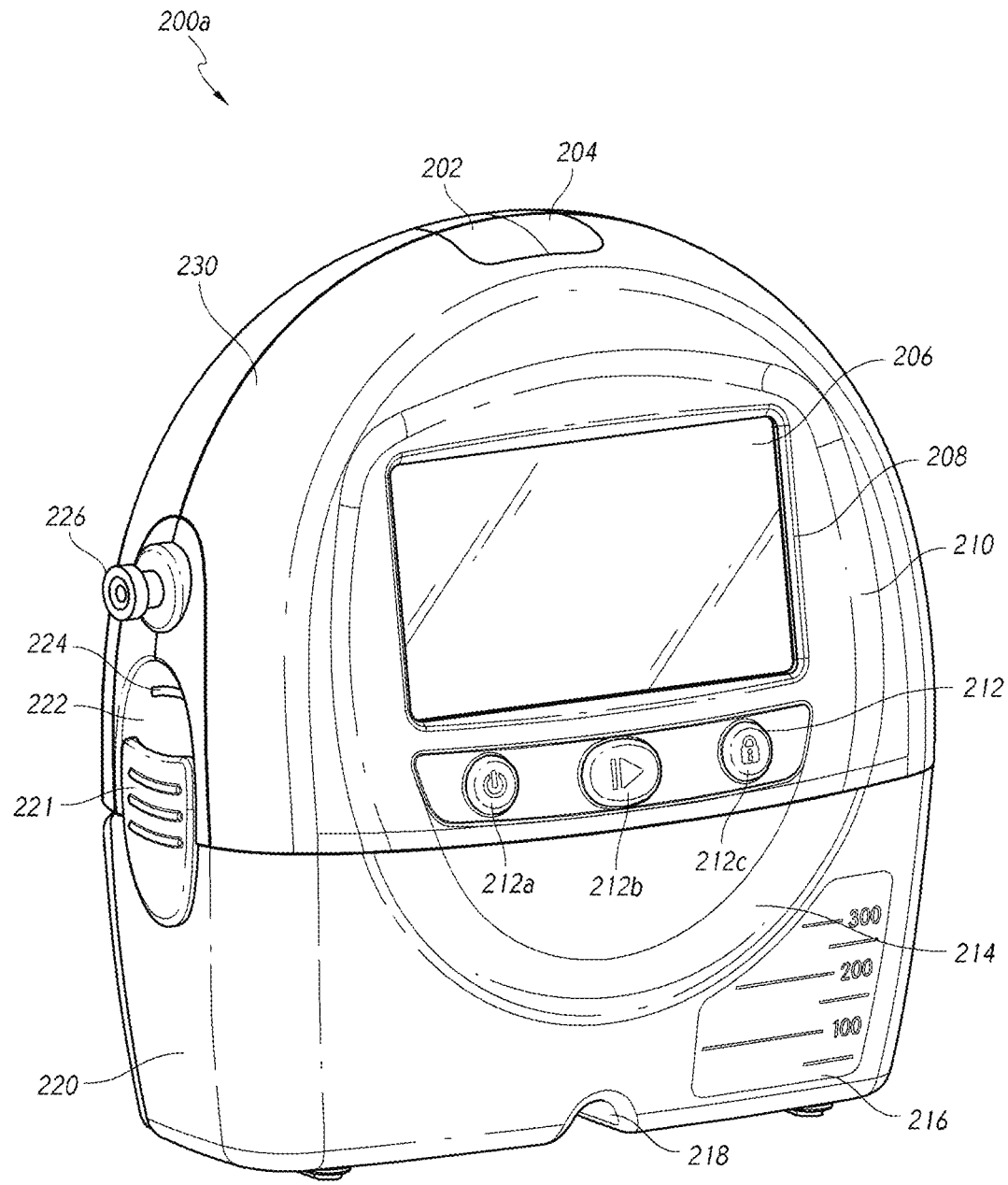
FIGS. 2A-2E illustrate a pump assembly and canister according to some embodiments.

FIG. 2A illustrates a front view 200A of a pump assembly 230 and canister 220 according to some embodiments. As is illustrated, the pump assembly 230 and the canister are connected, thereby forming a device. The pump assembly 230 comprises one or more indicators, such as visual indicator 202 configured to indicate alarms and visual indicator 204 configured to indicate status of the TNP system. The indicators 202 and 204 can be configured to alert a user to a variety of operating and/or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. In some embodiments, the pump assembly 230 can comprise additional indicators. In some embodiments, a single indicator is used. In other embodiments, multiple indicators are used. Any suitable indicator can be used such as visual, audio, tactile indicator, and so on. The indicator 202 can be configured to signal alarm conditions, such as canister full (or dressing full in case of a canisterless system), power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 comprises a display or screen 206 mounted in a recess 208 formed in a case of the pump assembly. In some embodiments, the display 206 can be a touch screen display. In some embodiments, the display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. In some embodiments, the canister 220 can be replaced with another canister, such as when the canister 220 has been filled with exudate. The canister 220 can include solidifier material.

The pump assembly 230 comprises one or more keys or buttons 212 configured to allow the user to operate and monitor the operation of the TNP system. As is illustrated, in some embodiments, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 and/or the buttons 212. For instance, button 212e can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. In some embodiments, multiple key presses and/or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted and/or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. The canister 220 comprises a tubing channel 218 for connecting to the conduit 140. In some embodiments, various of these features, such as the gripping portion 214, are omitted and/or various additional features are added to the canister 220.

Figure 2B:
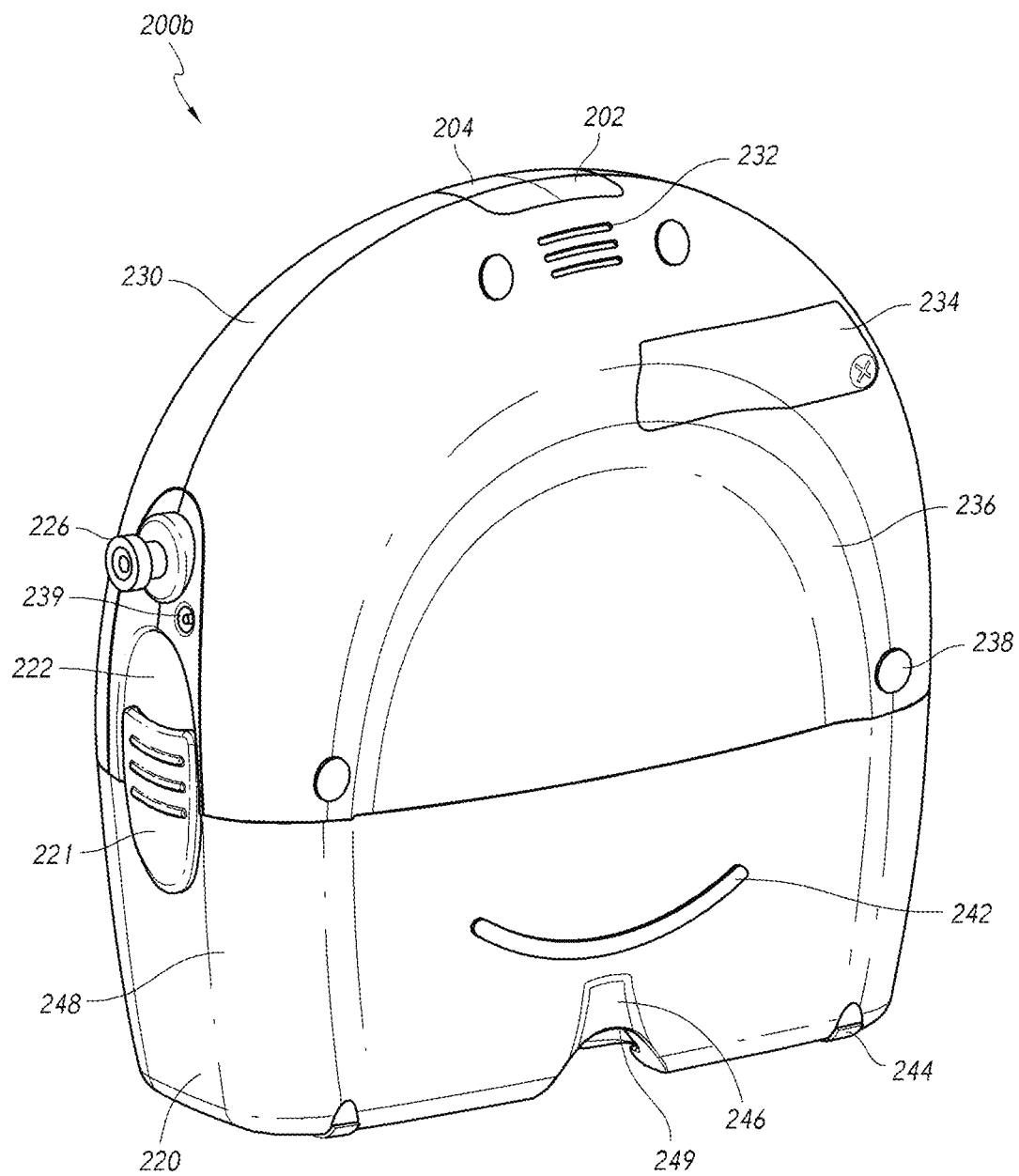

FIG. 2B illustrates a rear view 200B of the pump assembly 230 and canister 220 according to some embodiments. The pump assembly 230 comprises a speaker port 232 for producing and/or radiating sound. The pump assembly 230 includes a filter access door 234 for accessing and replacing one or more filters, such as odor filter, antibacterial filters, etc. In one embodiment, the access door 234 can be used to access a chamber (such as a plenum chamber) in which noise suppressing or sound absorbing material is placed. The chamber and sound absorbing material can be part of a silencing system that is used to suppress or absorb noise generated by the source of negative pressure. Sound absorbing material can serve to break up sound waves as travel (or reverberate) through the chamber. Sound absorbing material can further function as an odor suppressant. In one embodiment, for example, sound absorbing material can be impregnated with activated charcoal for odor suppression. The access door 234 can further include a seal (such as a sealing gasket) for tight closure of the chamber. Additional details of the silencing system are described in U.S. Patent Publication No. 2010/0185165, which is incorporated by reference in its entirety.

The pump assembly 230 comprises a gripping portion 236 formed in the case of the pump assembly. As is illustrated, the gripping portion 236 is a recess formed in the outer casing of the pump assembly 230. In some embodiments, the gripping portion 236 may include rubber, silicone, etc. coating. The gripping portion 236 can be configured (e.g., positioned and dimensioned) to allow the user to firmly hold the pump assembly 230, such as during removal of the canister 220. The pump assembly 230 includes one or more covers 238 configured as screw covers and/or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. In some embodiments, the power jack 239 is a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
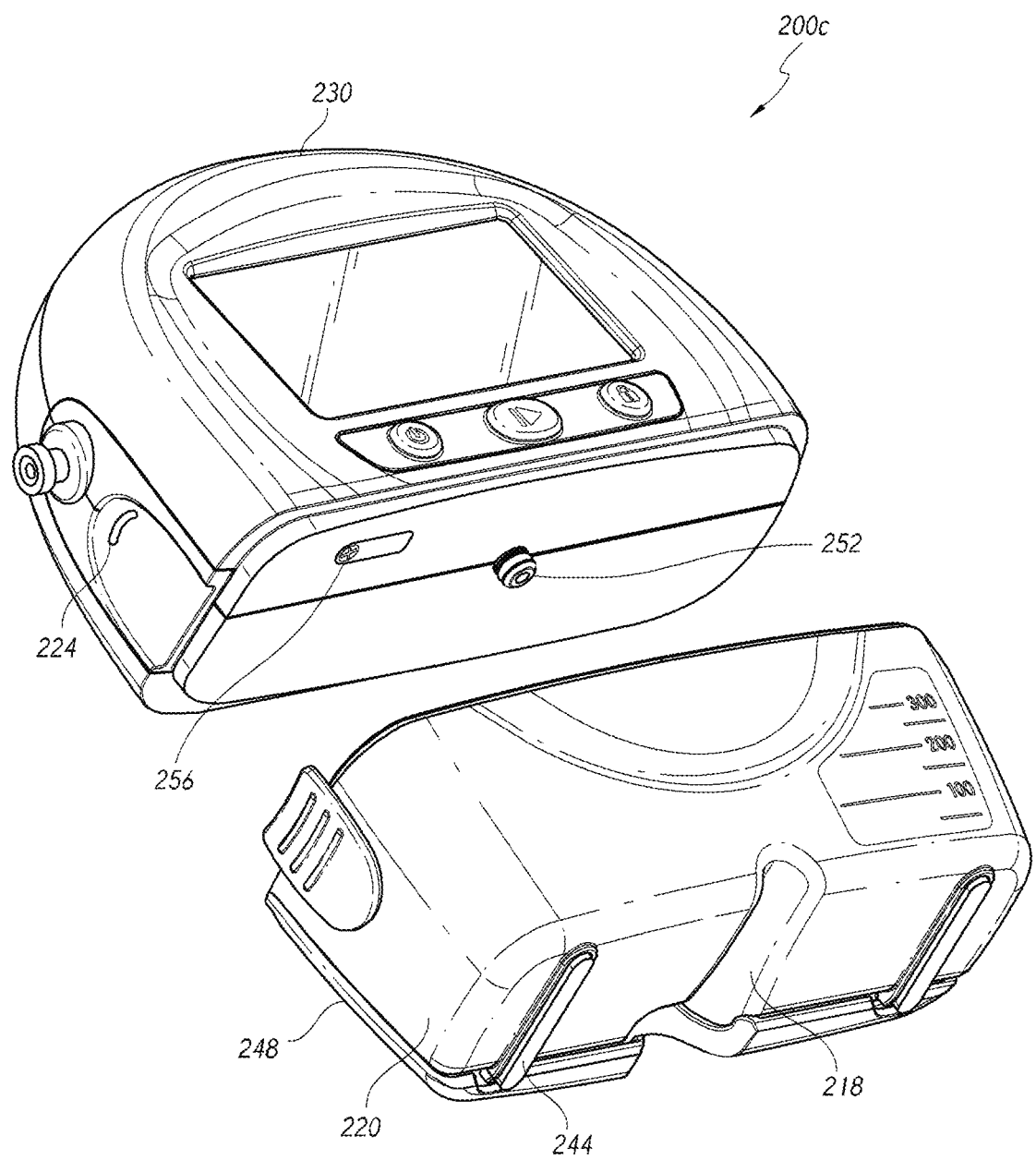

FIG. 2C illustrates a view 200C of the pump assembly 230 separated from the canister 220 according to some embodiments. The pump assembly 230 includes a vacuum attachment or connector 252 through which a vacuum pump communicates negative pressure to the canister 220. The connector 252 can correspond to the inlet of the pump assembly. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, and/or hybrid data transfer interfaces, such as SD, Compact Disc (CD), DVD, FireWire, Thunderbolt, PCI Express, and the like. In other embodiments, one or more of these additional ports are accessed through the door 234.

Figure 2D:
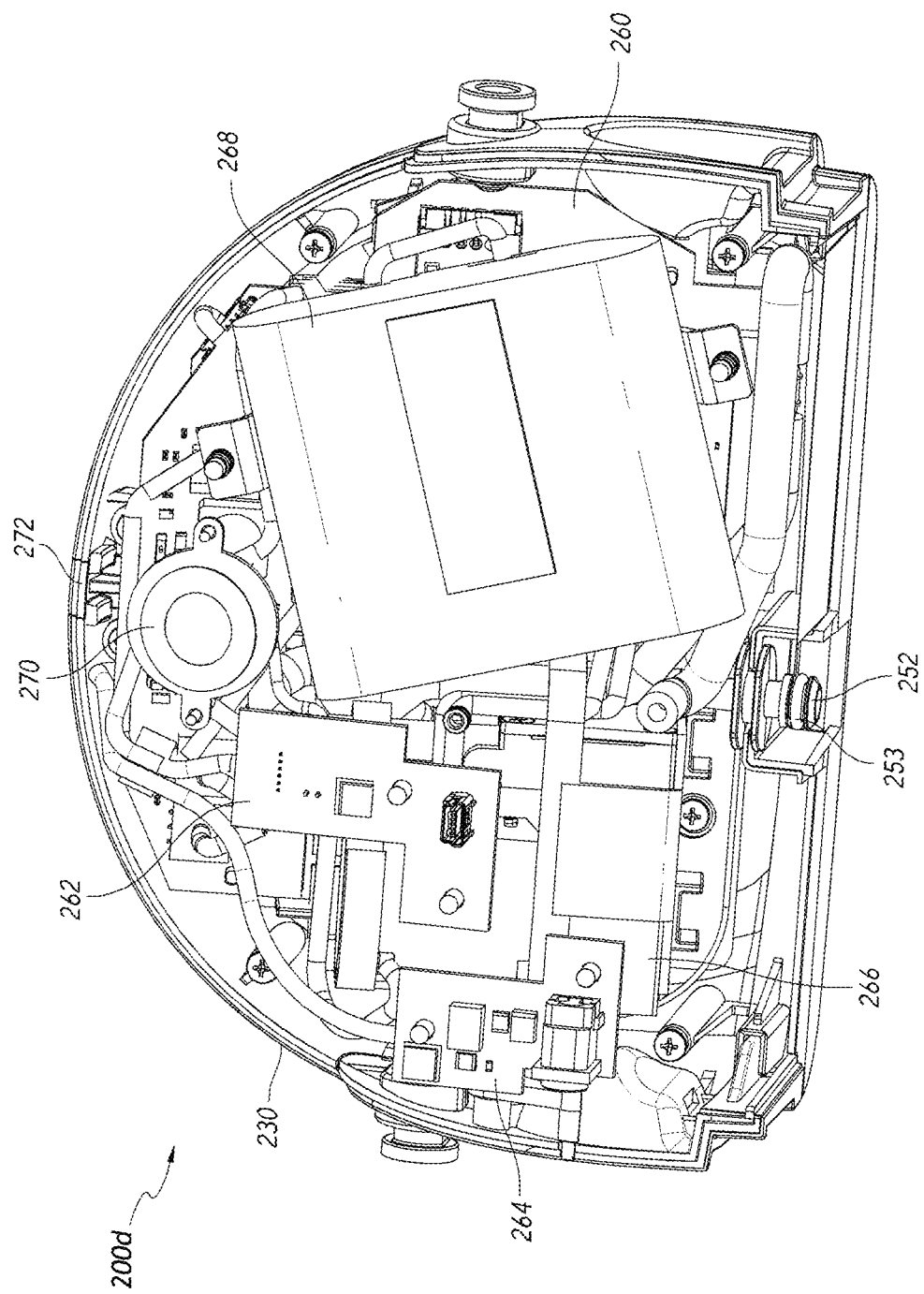

FIG. 2D illustrates a view 200D of the interior components of the pump assembly 230 according to some embodiments. The pump assembly 230 can include various components, such as a canister connector 252 which includes a sealing ring 253, control printed circuit board (PCB) 260, peripherals PCB 262 (e.g., for USB connectivity), power supply PCB 264, vacuum pump 266, power supply 268 (e.g., rechargeable battery), speaker 270, and light guide or pipe 272 (e.g., for status indication using guided light emitted by one or more LEDs). Further details of status indication are provided in U.S. Pat. No. 8,294,586, which is incorporated by reference in its entirety. Other components can be included, such as electrical cables, connectors, tubing, valves, filters, fasteners, screws, holders, and so on. In some embodiments, the pump assembly 230 can comprise alternative or additional components.

Figure 2E:
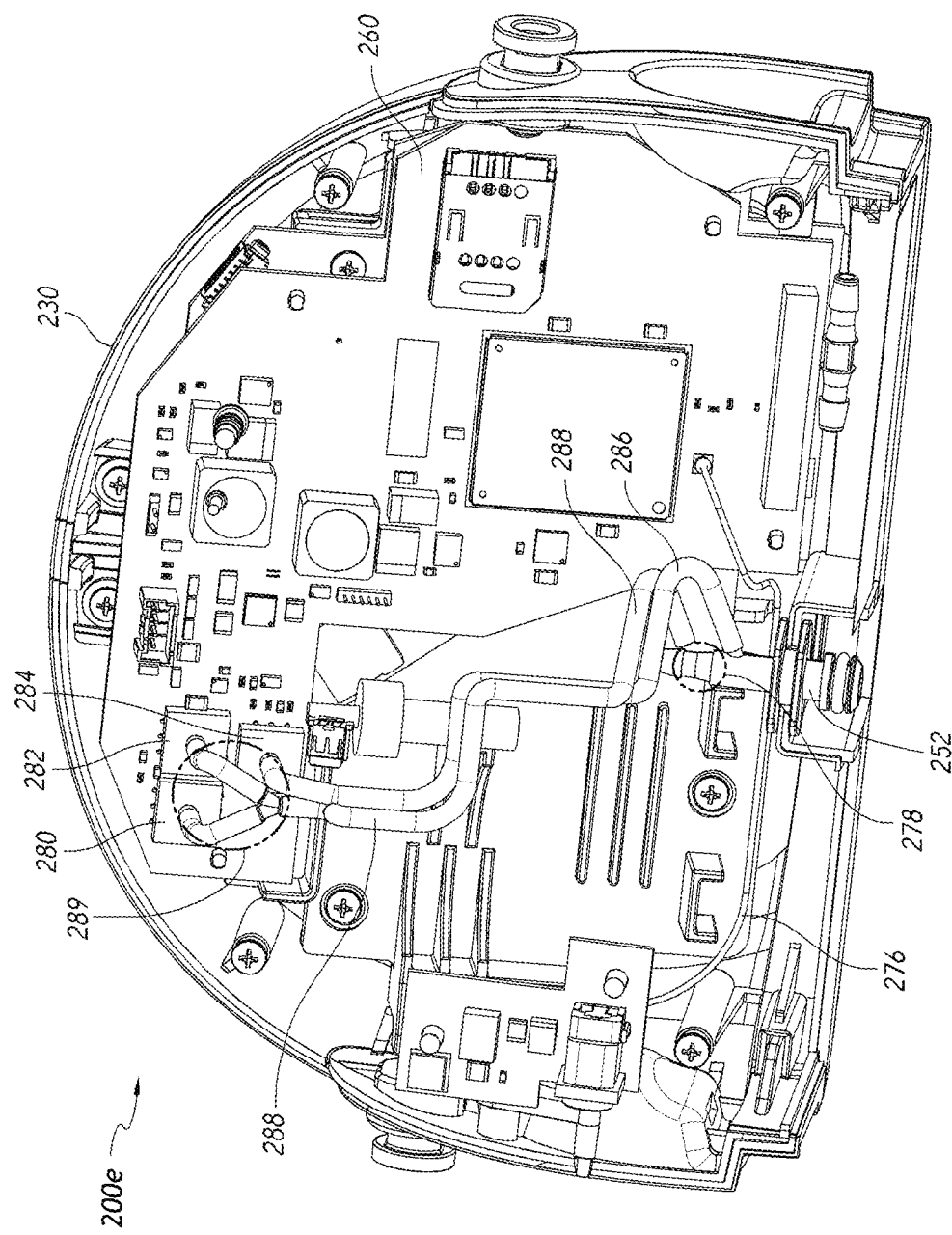

FIG. 2E illustrates another view 200E of the interior components of the pump assembly 230 according to some embodiments. As is explained below, the pump assembly 230 includes an antenna 276. The connector 252 between the vacuum pump 266 and the canister 220 includes a flow restrictor 278. As is explained below, the flow restrictor 278 can be a calibrated flow restrictor used for measuring flow in the fluid flow path and for determining various operating conditions, such as leaks, blockages, high pressure (over-vacuum), and the like. In some embodiments, flow across the restrictor 278 can be determined by measuring a pressure differential (or pressure drop) across the flow restrictor. In various embodiments, flow across the restrictor 278 can be characterized as high flow (e.g., due to a leak), low flow (e.g., due to a blockage or canister being full), normal flow, etc. As is illustrated, pressure sensor 284 measures pressure upstream (or on the canister side) of the flow restrictor 278. Pressure sensor 284 can be an electronic pressure sensor mounted on the control PCB 264. Conduit or lumen 286 can connect the upstream side of the flow restrictor 278 with the pressure sensor 284. Pressure sensors 280 and 282 measure pressure downstream (or on the vacuum pump side) of the flow restrictor 278. Pressure sensors 280 and 282 can be electronic pressure sensors mounted on the control PCB 264. Conduit or lumen 288 can connect the downstream side of the flow restrictor 278 with the pressure sensors 280 and 284 via a Y-connector 289.

In some embodiments, one of pressure sensors 280 and 282 can be designated as a primary pressure sensor and the other as a backup pressure sensor in case the primary pressure sensor becomes defective or inoperative. For example, pressure sensor 280 can be the primary pressure sensor and pressure sensor 282 can be the backup pressure sensor. Pressure drop across the flow restrictor 278 can be determined by subtracting pressure measured by sensor 280 and sensor 284. If pressure sensor 280 fails, pressure drop across the flow restrictor can be determined by subtracting pressure measured by sensor 282 and sensor 284. In certain embodiments, the backup pressure sensor can be used for monitoring and indicating high pressure conditions, that is when the pressure in the flow path exceeds a maximum pressure threshold. In some embodiments, one or more differential pressure sensors can be used. For example, a differential pressure sensor connected to the upstream and downstream sides of the flow restrictor 278 can measure the pressure drop across the flow restrictor. In some embodiments, one or more of these components, such as the flow restrictor 278, are omitted and/or additional components, such as one or more flow meters, are used.

Flow Rate Monitoring

Figure 3:
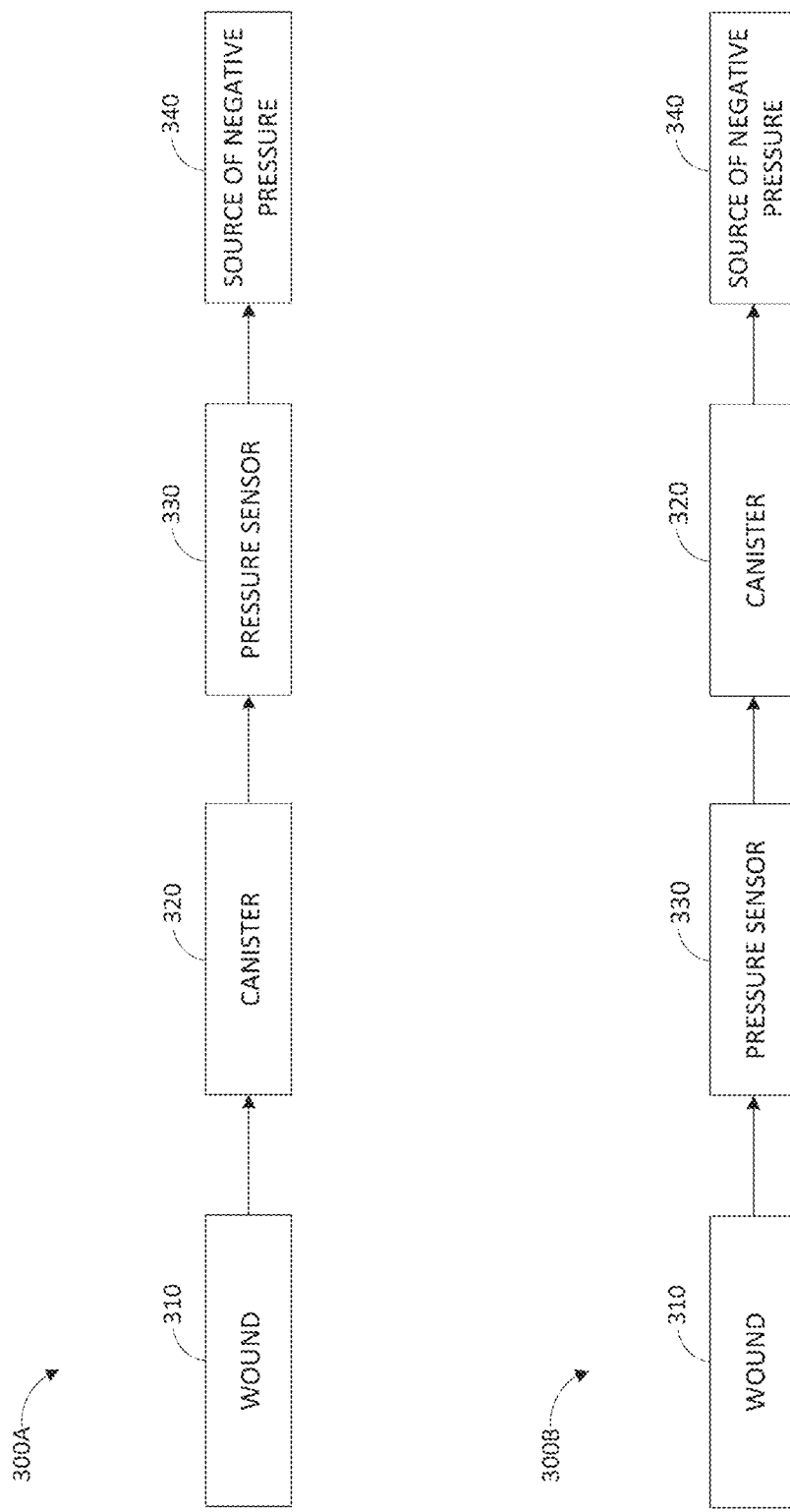
FIG. 3 illustrates fluid flow paths according to some embodiments.

FIG. 3 illustrates a fluid flow path 300A according to some embodiments. The flow path 300A includes a wound cavity 310, canister 320, pressure sensor 330, and source of negative pressure 340. The flow of fluid is from left to right (e.g., from the wound 310 to the negative pressure source 340). FIG. 3 illustrates a fluid flow path 300B according to some embodiments. The flow path 300B includes the wound 310 cavity, pressure sensor 330, canister 320, and source of negative pressure 340. The flow of fluid is from left to right (e.g., from the wound cavity 310 to the negative pressure source 340). As is illustrated, the difference between flow paths 300A and 300B is the positioning of the pressure sensor 330. In fluid flow path 300A the pressure sensor 330 is located downstream of the canister 320 (e.g., at the inlet of the negative pressure source 340), while in the fluid flow path 300B the pressure sensor 330 is located upstream of the canister 320.

Some embodiments of the system monitor and/or determine a rate of flow of fluid in the system. In certain embodiments, flow rate monitoring can be performed by a controller or processor. Monitoring the flow rate can be used, among other things, to ensure that therapy is properly delivered to the wound, to detect blockages, canister full (or dressing full in case of a canisterless system) conditions, and/or leaks in the fluid flow path, high pressure, ensure that the flow rate is not unsafe (e.g., dangerously high), etc.

In some embodiments, the system performs flow rate monitoring indirectly by measuring and/or monitoring activity of the negative pressure source. For example, speed of vacuum pump motor can be measured, such as, by using a tachometer. A pump control processor can continuously monitor the pump speed using the tachometer feedback from the pump. If pump speed falls below a threshold value over a particular period of time, such as 2 minutes, it can be determined that a blockage is present in the flow path, particularly in systems in which an minimum pump speed is expected (e.g., due to a presence of a controlled leak). The blockage can be due to a blockage in a tube or lumen, canister (or dressing) being full, etc. An alarm can be triggered and the system can wait for the user to take one or more actions to resolve the blockage. In some embodiments, activity of the negative pressure source can be measured by one or more other suitable techniques, such as by using a pump speed sensor (e.g., Hall sensor), measuring back EMF generated by the pump motor, and the like. A pump control processor can continuously monitor voltage and/or current at which the pump is being driven, and determine the activity of the negative pressure source based on the monitored voltage and/or current and load on the pump. In some embodiments, pulse frequency (e.g., pressure signal frequency) can be monitored (e.g., using one or more pressure sensors) to determine the activity of the negative pressure source. For example, a count of pressure pulses can be used as an indicator of the activity of the negative pressure source.

In various embodiments, tachometer can be read periodically, such as every 100 msec, and periodic readings made over a time duration, such as 2.5 seconds, 32 second, or any other suitable duration can be combined (e.g., averaged). Combined tachometer readings can be used for leak detection, blockage detection, limiting the maximum flow rate, etc. Combined tachometer readings (e.g., in counts) can be converted to a flow rate (e.g., in mL/min) using one or more conversion equations and/or tables so that a current flow rate is determined. In some embodiments, the flow rate is determined according to the following equation:

$$FR = C_1 * F * P + C_2$$

where FR is the flow rate, F is the frequency of the pump tachometer signal, P is pressure produced by the pump (or pressure setpoint), and $C_1$ and $C_2$ are suitable constants. The determined flow rate can be compared to various flow rate thresholds, such as blockage threshold, leakage threshold, and maximum flow rate threshold, to determine a presence of a particular condition, such as a blockage, leakage, and over-vacuum.

Other suitable ways for determining flow rate can be used. For example, the flow rate can be periodically computed, such as every 250 milliseconds or any other suitable time value, according to the following formula:

$$FR = Slope * Tachometer + Intercept$$

where Tachometer is an average of tachometer readings (e.g., in Hz), such as over last 2.5 second or any other suitable period of time, and Slope and Intercept are constants that are based on the pressure setpoint. The values for Slope and Intercept can be determined for possible pressure setpoints (e.g., −25 mmHg, −40 mmHg, −50 mmHg, 60 mmHg, −70 mmHg, −80 mmHg, −90 mmHg, −100 mmHg, −120 mmHg, −140 mmHg, 160 mmHg, −180 mmHg, −200 mmHg) for a given vacuum pump type. The flow as a function of the pump speed may not be a best fit as a single line because the vacuum pump can be designed to be more efficient at lower flow rates. Because of this, slope and intercept values can be pre-computed for various setpoints and various pumps. Flow rate can be measured in standard liters per minute (SLPM) or any other suitable measurement unit.

In some embodiments, a blockage condition is detected when the determined flow rate falls below a blockage threshold. A blockage alarm can be enabled if the blockage condition is present over a period of time, such as 30 seconds. The blockage alarm can be disabled when the determined flow rate exceeds the blockage threshold. In some embodiments, the system can differentiate between a blockage in a tube or lumen and canister (or dressing) full conditions. In some embodiments, a leakage condition is detected when the determined flow rate exceeds a leakage threshold. A leakage alarm can be enabled if the leakage condition is present over a period of time, such as 30 seconds. The leakage alarm can be disabled when the detected flow rate falls below the leakage threshold. In some embodiments, in order to prevent an over-vacuum condition, a maximum flow rate is imposed, such as 1.6 liters/min. Pump drive signal, such as voltage or current signal, can be limited not exceed the flow rate threshold.

In certain embodiments, one or more pressure sensors can be placed in suitable locations in the fluid flow path. Pressure measured by the one or more sensors is provided to the system (e.g., pump control processor) so that it can determine and adjust the pump drive signal to achieve a desired negative pressure level. The pump drive signal can be generated using PWM. Additional details of flow rate detection and pump control are provided in U.S. Patent Application No. 2013/0150813, which is incorporated by reference in its entirety.

In some embodiments, flow rate monitoring is performed by measuring flow through a flow restrictor placed in a portion of the fluid flow path. In certain embodiments, flow restrictor 278 illustrated in FIG. 2E can be used. The flow restrictor can be calibrated such that it can be used to reliably monitor flow rate for different types of wounds, dressings, and operating conditions. For example, a high precision silicon flow restrictor can be used. As another example, the flow restrictor can be built using other suitable materials. The flow restrictor can be located at any suitable location in the flow path, such as between the source of the negative pressure and the canister, such as upstream of the source of the negative pressure and downstream of the canister. A differential pressure sensor or two pressure sensors can be used to measure a pressure drop across the flow restrictor. For example, as explained above in connection with FIG. 2E, the pressure drop across the flow restrictor 278 can be measured using sensors 282 and 284. In certain embodiments, if the pressure drop falls below a pressure differential threshold, which indicates low flow, the measured flow rate is compared to a flow rate threshold. If the measured flow rate falls below the flow rate threshold, blockage condition is detected. Additional details of blockage detection are provided in U.S. Patent Publication No. 2011/0071483, which is incorporated by reference in its entirety. In some embodiments, the measured flow rate is compared to a leakage threshold. If the measured flow rate exceeds the leakage threshold, a leak is detected. Additional details of leakage detection are provided in U.S. Pat. No. 8,308,714, which is incorporated by reference in its entirety.

Blockage Detection

Figure 4:
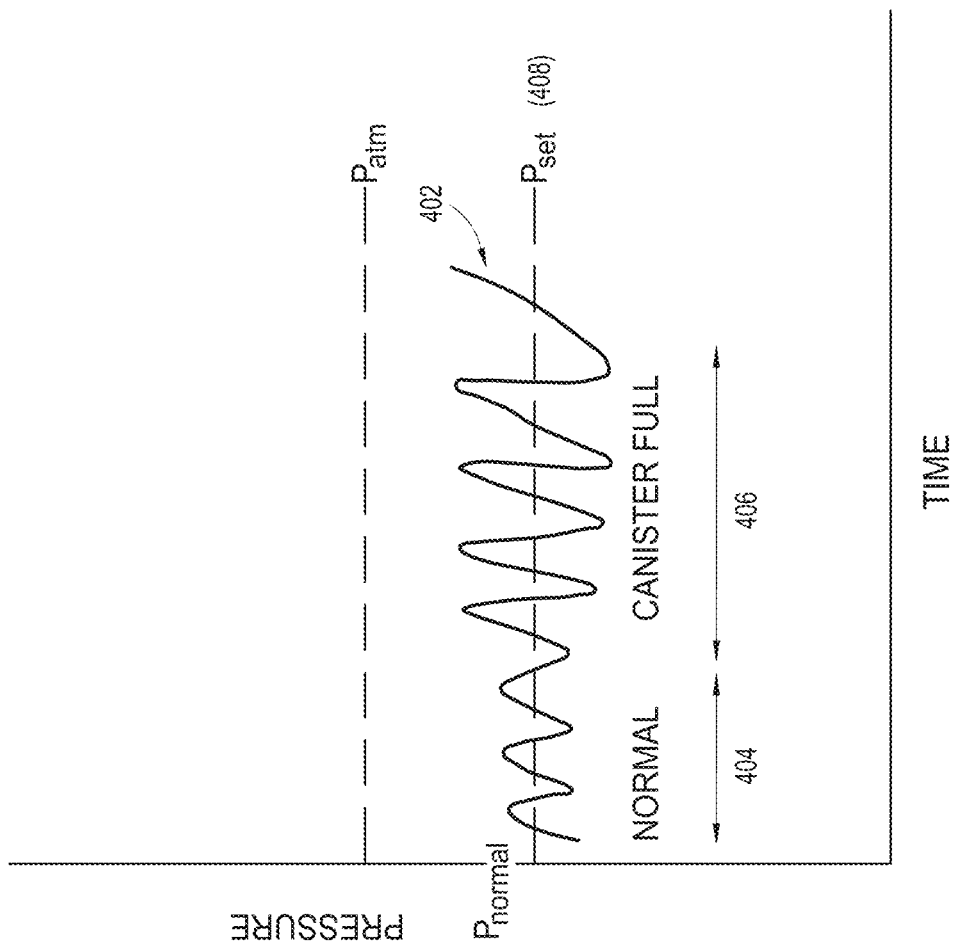
FIG. 4 illustrates a graph of pressure signals according to some embodiments.

In some embodiments, blockages and presence of exudate in one or more tubes or lumens are detected by processing data from one or more pressure sensors, such as sensors 280, 282, and 284. This detection can be enhanced by changing one or more settings of the vacuum pump, such as increasing vacuum level delivered by the pump, decreasing the vacuum level, stopping the pump, changing the pump speed, changing a cadence of the pump, and the like. In some embodiments, as the pump operates, it generates pressure pulses or signals that are propagated through the fluid flow path. The pressure signals are illustrated in the pressure curve 402 of FIG. 4 according to some embodiments. As is illustrated in region 404, pressure in the fluid flow path varies or oscillates around a particular pressure setting or set point 408 (e.g., as selected by the user) during normal operation of the system. Region 406 illustrates pressure pulses in the flow path when there is a blockage distal to the negative pressure source, such as the canister (or dressing) becomes full and/or a canister filter is occluded or blocked. As is illustrated, a distal blockage causes a reduced volume to be seen upstream of the canister (or dressing), and the amplitude of the pressure pulses increases. The frequency of a pressure signal is slowed or decreased in some embodiments. In certain embodiments, this change or "bounce" in the magnitude (or frequency) of the pressure pulse signal can be magnified or enhanced by varying the pump speed, varying the cadence of the pump, such as by adjusting PWM parameters, and the like. Such adjustments of pump operation are not required but can be performed over short time duration and the changes can be small such that the operation of the system remains relatively unaffected. In some embodiments, the canister filter can be hydrophobic so that the flow of liquid is substantially blocked while the flow of air is allowed. Additional details of flow rate detection are described in U.S. Patent Publication No. 2012/0078539, which is incorporated by reference in its entirety.

In some embodiments, canisterless systems use absorbent dressing for exudate removed from the wound. Such dressing may include absorbing or superabsorbing material to collect and/or retain exudate so that it is not aspirated into the negative pressure source. Similar to a canister filter, a dressing filter (which may be hydrophobic) may be used to prevent the exudate from reaching the negative pressure source. In such systems, detection of a dressing full condition or dressing filter (which may be) occluded condition can be an equivalent to detection of a canister full condition.

In some embodiments, changes in characteristics of pressure signals can be used to determine distal blockages, level of exudate in the canister (or dressing), canister (or dressing) full conditions, and the like. The characteristics can include signal magnitude, frequency, shape (e.g., envelope), etc. In some embodiments, the system can detect canister (or dressing) pre-full condition or the level of exudate in the canister (or dressing) reaching a certain threshold, which may be less than being approximately 100% full. For example, the system can detect the canister (or dressing) being 75% full, 80% full, 95%, and so on. Advantageously, such detection mechanisms can provide earlier indication of the need to change the canister (or dressing) and avoid prolonged interruption of the delivery of therapy. Sensitivity of alarms can be increased. In various embodiments, the level of a leak in present in the fluid flow path does not affect accurate determination of the level of exudate in the canister and/or detection of the canister (or dressing) pre-full or full conditions.

Figure 5A:
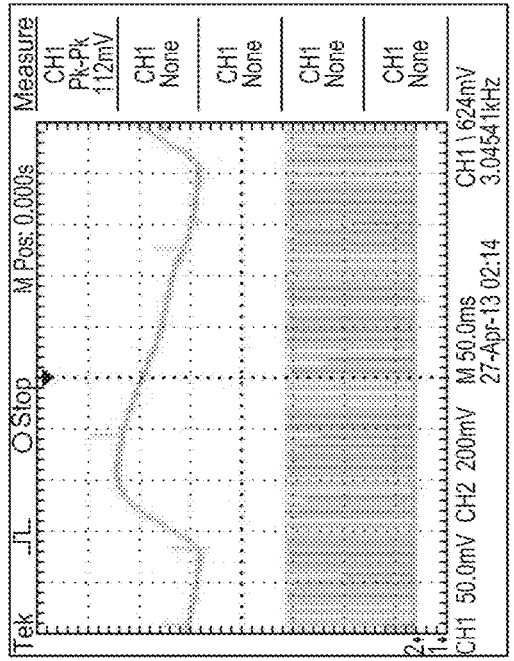
FIGS. 5A-5D illustrate graphs of pressure signals according to some embodiments.

FIGS. 5A-5D illustrates graphs of pressure signals according to some embodiments. The illustrated graphs can correspond to a particular pressure setting, such as 40 mmHg. The illustrated graphs can also correspond to various leak levels of leak rates in the system. For example, FIG. 5A may correspond to 60 mL/min leak (e.g., low leak), FIG. 5B may correspond to a 150 mL/min leak, FIG. 5C may correspond to a 450 mL/min leak, and FIG. 5D may correspond to a 1000 mL/min leak (e.g., very high leak). FIG. 5A illustrates a magnitude curve 502A of the pressure signal in the flow path as sensed by one or more pressure sensors over a period of time. Curve 502A can correspond to a signal observed when the canister is relatively empty. For example, the canister may be configured to hold up to 750 mL fluid volume, and curve 502A can correspond to the empty volume of 515 mL. As is illustrated, the bounce in the pressure signal magnitude curve 502A is relatively small as the curve is substantially flat. The bounce of the pressure signal can be measured using a variety of techniques, such as by measuring peak-to-trough change and selecting the largest such change as being indicative of the largest bounce. Curve 502A can correspond to the voltage reading, current reading, etc. Curve 504A corresponds to a pump speed signal (e.g., as measured by a tachometer, PWM signal, etc.).

Figure 5B:
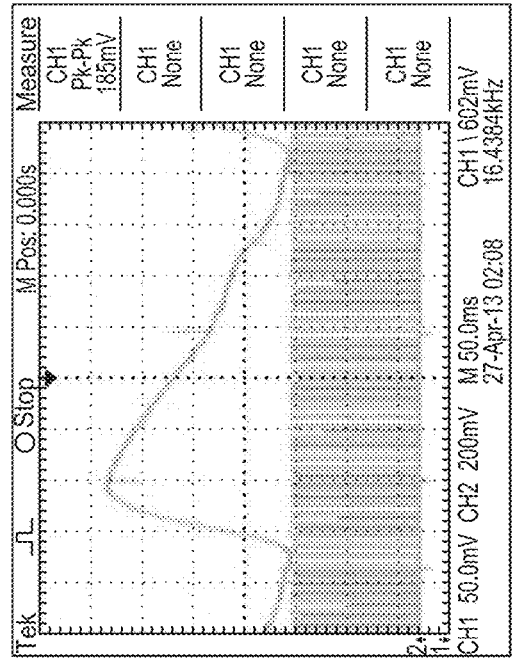
Figure 5C:
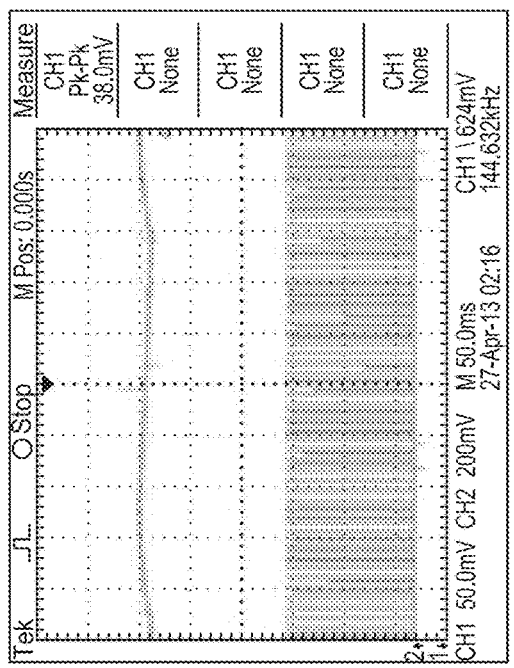

FIG. 5B illustrates a magnitude curve 502B of the pressure signal in the flow path as sensed by one or more pressure sensors over a period of time. Curve 502B can correspond to a signal observed when the canister is relatively full. For example, the canister may be configured to hold up to 750 mL volume, and curve 502B can correspond to the empty volume of 60 mL. As is illustrated, the bounce in the pressure signal magnitude curve 502B is larger than that in curve 502A. Curve 504B corresponds to the pump speed signal. FIG. 5C illustrates a magnitude curve 502C of the pressure signal in the flow path as sensed by one or more pressure sensors over a period of time. Curve 502C can correspond to a signal observed when the canister is almost full. For example, the canister may be configured to hold up to 750 mL volume, and curve 502C can correspond to the empty volume of 30 mL. As is illustrated, the bounce in the pressure signal magnitude curve 502B is larger than that in curves 502A and 502B. Curve 504C corresponds to the pump speed signal.

Figure 5D:
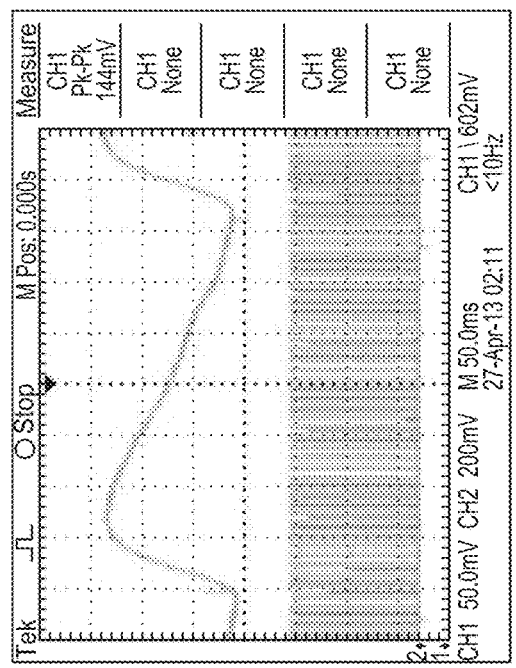
Figure 6A:
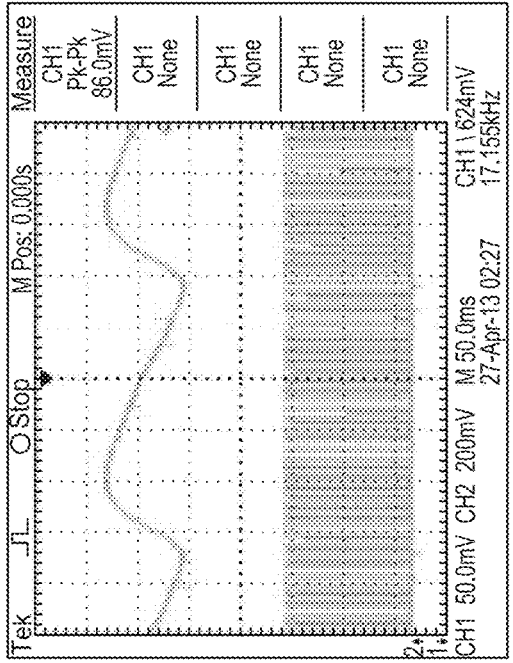
FIGS. 6A-6D illustrate graphs of pressure signals according to some embodiments.
Figure 6B:
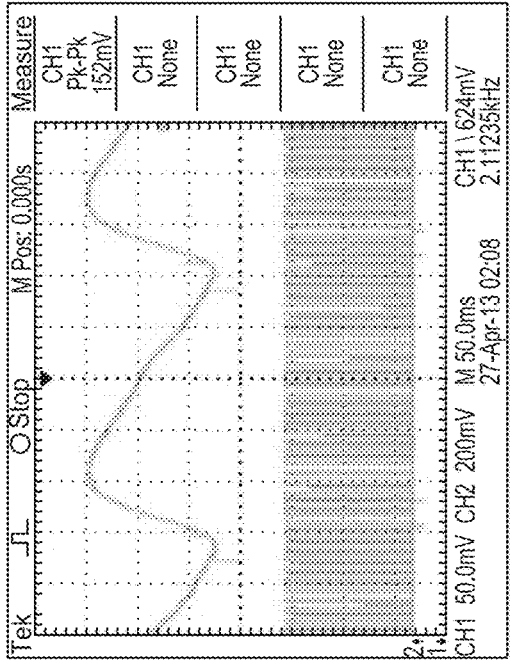
Figure 6C:
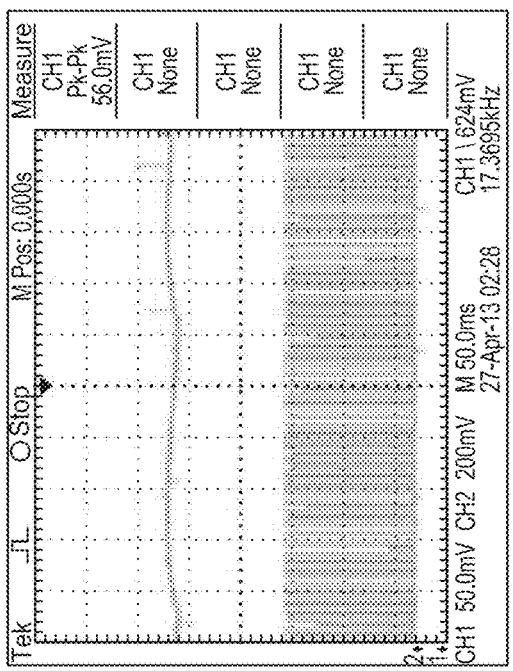
Figure 6D:
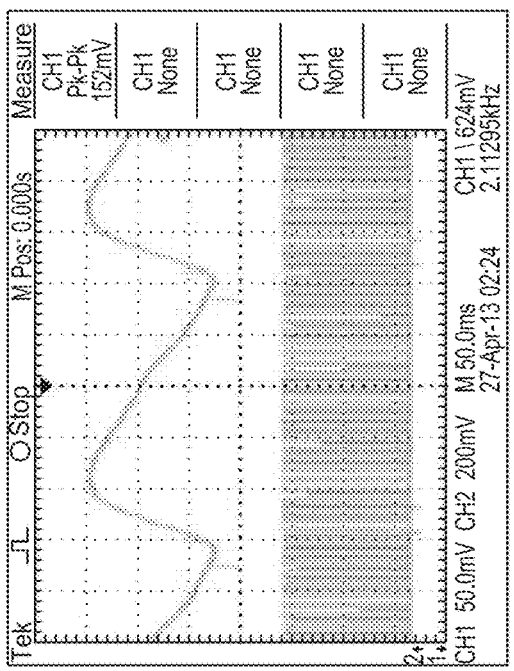
Figure 7A:
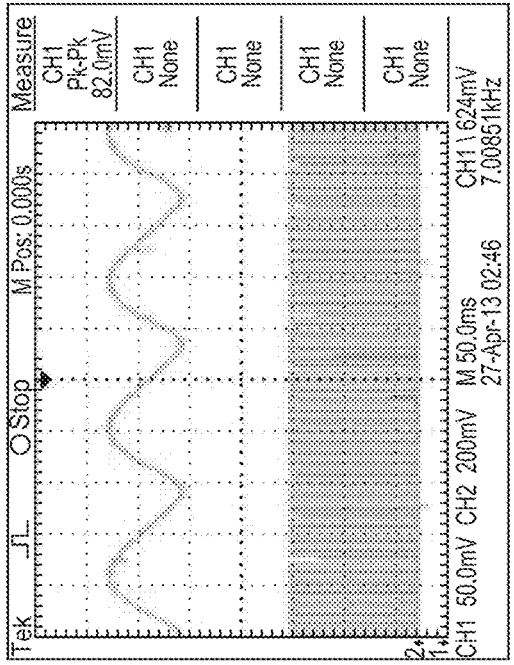
FIGS. 7A-7D illustrate graphs of pressure signals according to some embodiments.
Figure 7B:
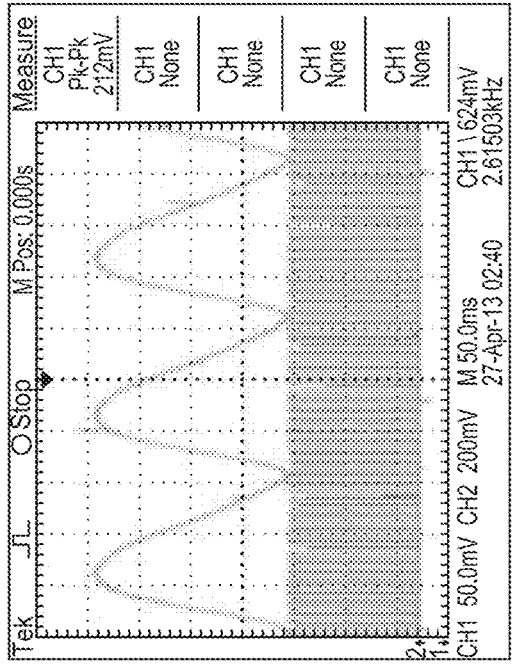
Figure 7C:
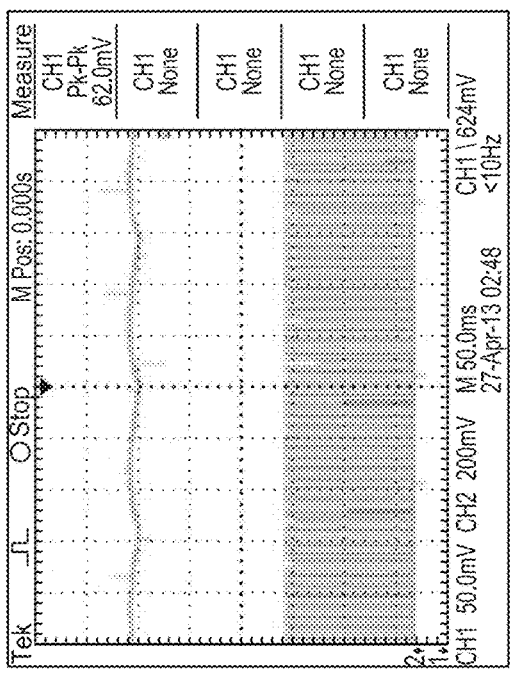
Figure 7D:
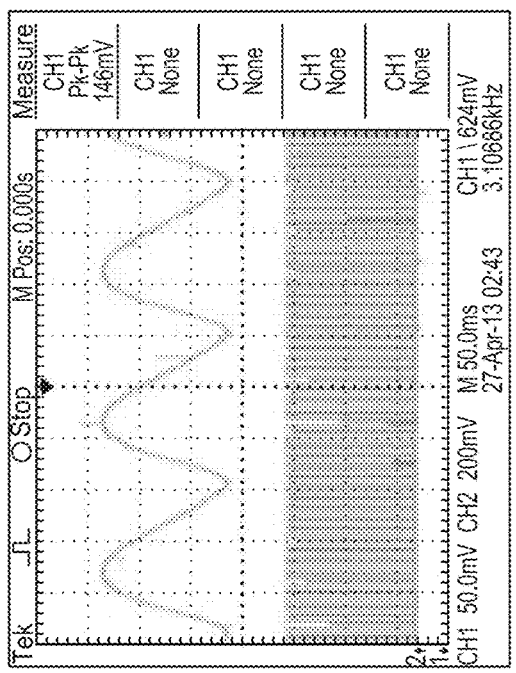
Figure 8A:
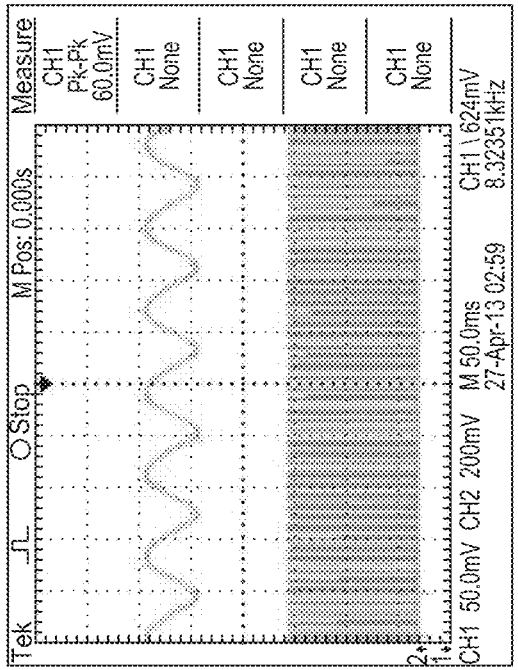
FIGS. 8A-8D illustrate graphs of pressure signals according to some embodiments.
Figure 8B:
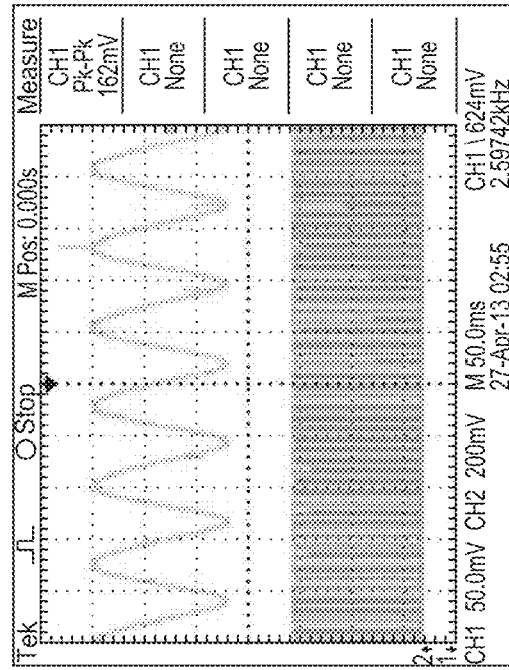
Figure 8C:
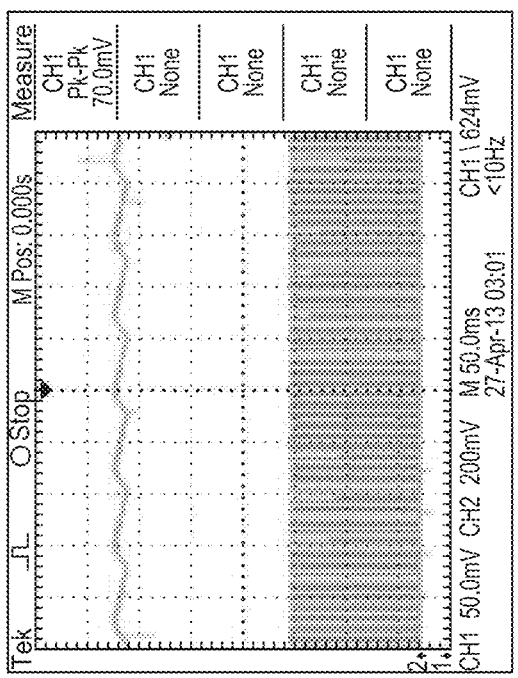
Figure 8D:
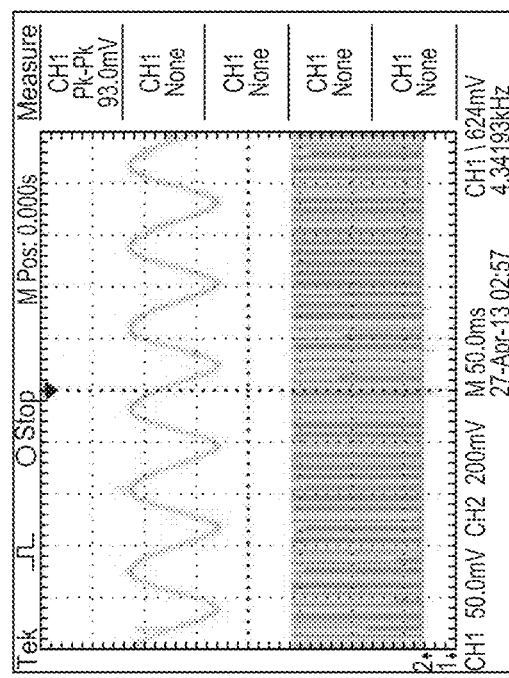

FIG. 5D illustrates a magnitude curve 502D of the pressure signal in the flow path as sensed by one or more pressure sensors over a period of time. Curve 502D can correspond to a signal observed when the canister is nearly full. For example, the canister may be configured to hold up to 750 mL volume, and curve 502D can correspond to the empty volume of 15 mL. As is illustrated, the bounce in the pressure signal magnitude curve 502D is larger than that in curves 502A, 502B, and 502C. Curve 504D corresponds to the pump speed signal.

Table 1 illustrates the largest magnitude bounces or peak-to-trough changes (e.g., in voltage as indicated by $V_{p-p}$) measured for the curves 502A, 502B, 502C, and 502D according to some embodiments. With reference to the first row (row 1), column A corresponds to curve 502A and indicates the largest change of 0.010 V, column B corresponds to curve 502D and indicates the largest change of 0.078 V, column C corresponds to curve 502C and indicates the largest change of 0.122 V, and column D corresponds to curve 502D and indicates the largest change of 0.170 V. These increasing bounce values confirm that the bounce in the pressure signal magnitude increases as the canister fills up. Level of exudate in the canister (or the dressing) can be detected by comparing the determined pressure magnitude bounce to one or more magnitude thresholds, which can be determined experimentally for canisters (or dressing) of various sizes. For example, canister (or dressing) pre-full condition may be set to the canister having 30 mL or less empty volume. Using Table 1, a pre-full threshold can be set to approximately 0.12 V peak-to-trough bounce. In some embodiments, measures other than or in addition to peak-to-trough can be used, such as average bounce, etc.

TABLE 1

Pressure Magnitude Bounce at 40 mmHg

| | Pressure Magnitude ($V_{p-p}$) at 40 mmHg | D 15 mL volume | C 30 mL volume | B 60 mL volume | A 515 mL volume |
|---|---|---|---|---|---|
| 1 | 60 mL/min | 0.170 | 0.122 | 0.078 | 0.010 |
| 2 | 150 mL/min | 0.174 | 0.120 | 0.074 | 0.012 |
| 3 | 450 mL/min | 0.178 | 0.118 | 0.068 | 0.008 |
| 4 | 1000 mL/min | 0.124 | 0.082 | 0.050 | 0.012 |

In some embodiments, signal processing techniques can be utilized on the detected pressure signal. For example, sensed pressure values can be processed, such as low-pass filtered (e.g., via averaging), to remove noise. As another example, detected pressure signal can be converted into frequency domain, for example by using the Fast Fourier Transform (FFT). The signal can be processed and analyzed in frequency domain.

FIGS. 6A-6D illustrates graphs of pressure signals according to some embodiments. Similar to FIGS. 5A-5D, these graphs illustrate pressure magnitude curves and pump speed curves at 150 mL/min leak for unfilled canister volumes of 515 mL, 60 mL, 30 mL, and 15 mL. As is illustrated in FIGS. 6A-6D and confirmed by the values in the second row (row 2) of Table 1, the bounce in the pressure signal increases as the canister fills up. FIGS. 7A-7D illustrates graphs of pressure signals according to some embodiments. Similar to FIGS. 5A-5D, these graphs illustrate pressure magnitude curves and pump speed curves at 450 mL/min leak for unfilled canister volumes of 515 mL, 60 mL, 30 mL, and 15 mL. As is illustrated in FIGS. 7A-7D and confirmed by the values in the third row (row 3) of Table 1, the bounce in the pressure signal increases as the canister fills up. FIGS. 8A-8D illustrates graphs of pressure signals according to some embodiments. Similar to FIGS. 5A-5D, these graphs illustrate pressure magnitude curves and pump speed curves at 1000 mL/min leak (which is a very high leak) for unfilled canister volumes of 515 mL, 60 mL, 30 mL, and 15 mL. As is illustrated in FIGS. 8A-8D and confirmed by the values in the fourth row (row 4) of Table 1, the bounce in the pressure signal increases as the canister fills up. From the illustrations in FIGS. 5-8 and the values in Table 1, it can be seen that detection of the level of exudate in the canister (or in the dressing) and/or canister (or dressing) pre-full condition can be performed irrespective of the leak rate in the fluid flow path.

Figure 9:
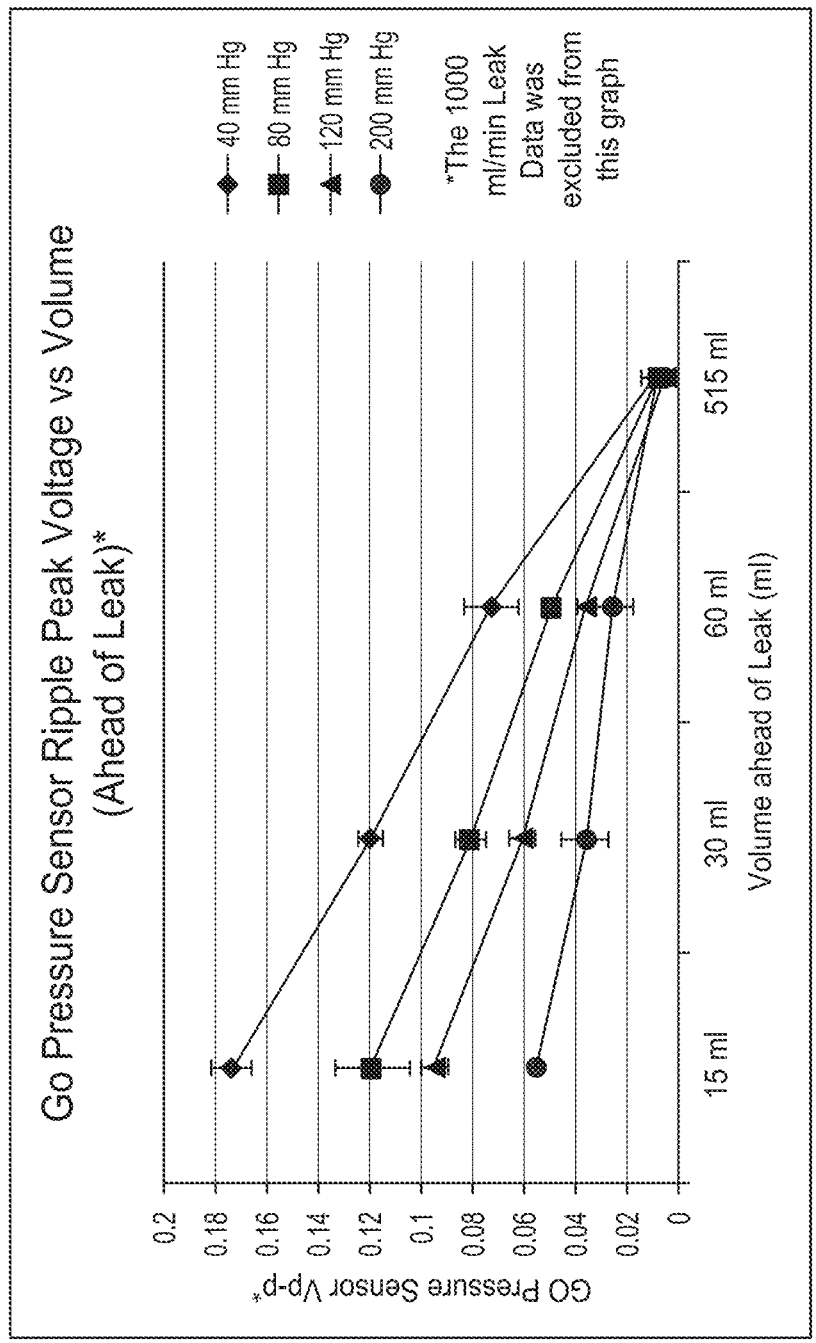
FIG. 9 illustrates sensed pressure magnitude ripple according to some embodiments.

As is illustrated in FIGS. 5-8 and Table 1, the bounce or ripple in the observed pressure magnitude increases as the canister fills up and the volume "seen" by the pump decreases. FIG. 9 illustrates sensed pressure magnitude ripple according to some embodiments. The y-axis represents largest peak-to-trough voltage changes. The x-axis corresponds to canister unfilled volumes (e.g., volume ahead or upstream of the pump). A 750 mL canister is used according to some embodiments. There are four curves illustrated corresponding to target pressure settings of 40 mmHg, 80 mmHg, 120 mmHg, and 200 mmHg. Vertical bars on the curves represent variation resulting from the changes to the leak rate. Table 2 illustrates the plotted values according to some embodiments. As is illustrated in FIG. 9 and Table 2, magnitude of the pressure bounce increases as the canister becomes full irrespective of the leak rate for various pressure settings.

TABLE 2

| $V_{p-p}$* | 15 mL volume | 30 mL volume | 60 mL volume | 515 mL volume |
|---|---|---|---|---|
| 40 mmHg | 0.174 ± 0.008 | 0.120 ± 0.004 | 0.073 ± 0.010 | 0.010 ± 0.004 |
| 80 mmHg | 0.119 ± 0.015 | 0.081 ± 0.006 | 0.049 ± 0.002 | 0.008 ± 0.000 |
| 120 mmHg | 0.095 ± 0.005 | 0.061 ± 0.005 | 0.037 ± 0.002 | 0.006 ± 0.000 |
| 200 mmHg | 0.056 ± 0.000 | 0.037 ± 0.009 | 0.027 ± 0.009 | 0.008 ± 0.000 |

(* 1000 mL/min data was excluded)

In some embodiments, thresholds for determining the level of exudate in the canister (or the dressing) and/or canister (or dressing) pre-full condition can be determined for various pressure settings and various canister volumes. For example, Table 3 illustrates the largest magnitude bounces or peak-to-trough changes for 80 mmHg pressure setting according to some embodiments. Similar tables can be constructed for other possible pressure settings. Level of exudate in the canister/dressing (and, accordingly, a measure of how empty the canister/dressing is), canister/dressing pre-full condition, and/or canister/dressing full condition can be determined at run time by loading a table corresponding to a particular selected pressure setting and comparing the monitored pressure signal magnitude bounce to one or more thresholds. Other suitable data structures can be used in place of a table, such as array, list, index, graph, etc.

TABLE 3

Pressure Magnitude Bounce at 80 mmHg

| | Pressure Magnitude ($V_{p-p}$) at 80 mmHg | D 15 mL volume | C 30 mL volume | B 60 mL volume | A 515 mL volume |
|---|---|---|---|---|---|
| 1 | 60 mL/min | 0.114 | 0.078 | 0.048 | 0.008 |
| 2 | 150 mL/min | 0.116 | 0.084 | 0.050 | 0.008 |
| 3 | 450 mL/min | 0.128 | 0.080 | 0.050 | 0.008 |
| 4 | 1000 mL/min | 0.092 | 0.058 | 0.034 | 0.010 |

In some embodiments, frequency of the detected pressure signal can be used in addition to or instead of changes in amplitude for detection of canister (or dressing) pre-full conditions and/or for determining the level of exudate in the canister (or dressing). For example, Table 4 illustrates pressure signal frequencies at 40 mmHg pressure setting for various unfilled canister volumes at various leak rates according to some embodiments. As is shown in Table 4, the frequency of the detected pressure signal decreases or drops as the canister becomes full (e.g., compare column A corresponding to 515 mL unfilled canister volume to column D corresponding to 15 mL unfilled canister volume). This change in the frequency is observed irrespective of the leak rate. The frequency of the detected pressure signal can be compared to one or more frequency thresholds, which may be determined experimentally, to detect canister (or dressing) pre-full condition and/or detect the level of exudate in the canister (or dressing).

TABLE 4

Pressure Signal Frequency at 40 mmHg

| Pressure Frequency at 40 mmHg (Hz) | D 15 mL volume | C 30 mL volume | B 60 mL volume | A 515 mL volume |
|---|---|---|---|---|
| 1 | 60 mL/min | 2.59 | 2.67 | 2.67 | 2.62 |
| 2 | 150 mL/min | 3.51 | 3.76 | 3.75 | 3.53 |
| 3 | 450 mL/min | 6.62 | 6.94 | 6.99 | 6.94 |
| 4 | 1000 mL/min | 13.16 | 12.99 | 12.66 | 13.89 |

In some embodiments, similar tables can be constructed for other possible pressure settings. For example, Table 5 illustrates pressure signal frequencies at 80 mmHg pressure setting for various unfilled canister volumes at various leak rates according to some embodiments. Level of exudate in the canister (or dressing), canister (or dressing) pre-full condition, and/or canister (or dressing) full condition can be determined at run time by loading a table (or another suitable data structure) corresponding to a particular selected pressure setting and comparing the monitored pressure signal frequency to one or more thresholds. The thresholds can be determined experimentally for various canister (or dressing) volumes.

TABLE 5

Pressure Signal Frequency at 80 mmHg

| Pressure Frequency at 80 mmHg (Hz) | D 15 mL volume | C 30 mL volume | B 60 mL volume | A 515 mL volume |
|---|---|---|---|---|
| 1 | 60 mL/min | 3.76 | 3.83 | 3.82 | 3.82 |
| 2 | 150 mL/min | 4.98 | 4.67 | 4.81 | 4.88 |
| 3 | 450 mL/min | 8.26 | 8.47 | 8.26 | 8.20 |
| 4 | 1000 mL/min | 15.38 | 15.63 | 15.15 | 15.87 |

In some embodiments, additional attributes can be used for canister (or dressing) pre-full detection and/or determination of the level of exudate in the canister (or dressing). For example, flow rate through the flow path can be used in addition to analyzing the pressure magnitude. In some embodiments, flow rate can be measured indirectly by measuring and analyzing the pump speed as is disclosed in U.S. Patent Publication No. 2012/0001762, which is incorporated by reference in its entirety. In some embodiments, flow rate can be measured directly by using a flow meter. In some embodiments, increase in the pressure magnitude bounce and decrease in the flow rate (e.g., pump speed, such as reflected by a slowing tachometer) indicates a canister (or dressing) full condition. Decrease in the pump speed alone may not be a reliable indicator of the canister full condition as such decrease can be caused by an improved seal and resulting lowering of the leak rate. In addition, presence of a small leak in the flow path may cause the pump to continue working even though the canister may be nearly full or frill, which can cause inaccurate detection of the canister full condition.

In some embodiments, detection of canister (or dressing) pre-full and/or full conditions using the characteristics of the pressure signals can allow the system to differentiate between blockage conditions in the fluid flow path and blockages in the canister (or in the dressing). In some embodiments, alarm sensitivity is improved. For example, canister full detection mechanisms in systems that do not use characteristics of the pressure signal may rely solely on the flow rate measurements (e.g., as indicated by pump speed measurements) for determining whether the canister is full. Using characteristics of the pressure signal as disclosed herein can trigger the canister frill alarm much earlier, such as for example 20 or more minutes earlier. Advantageously, improving alarm sensitivity can result in increasing safety and patient comfort as the canister can be changed timely before it becomes full and therapy is interrupted.

Figure 10:
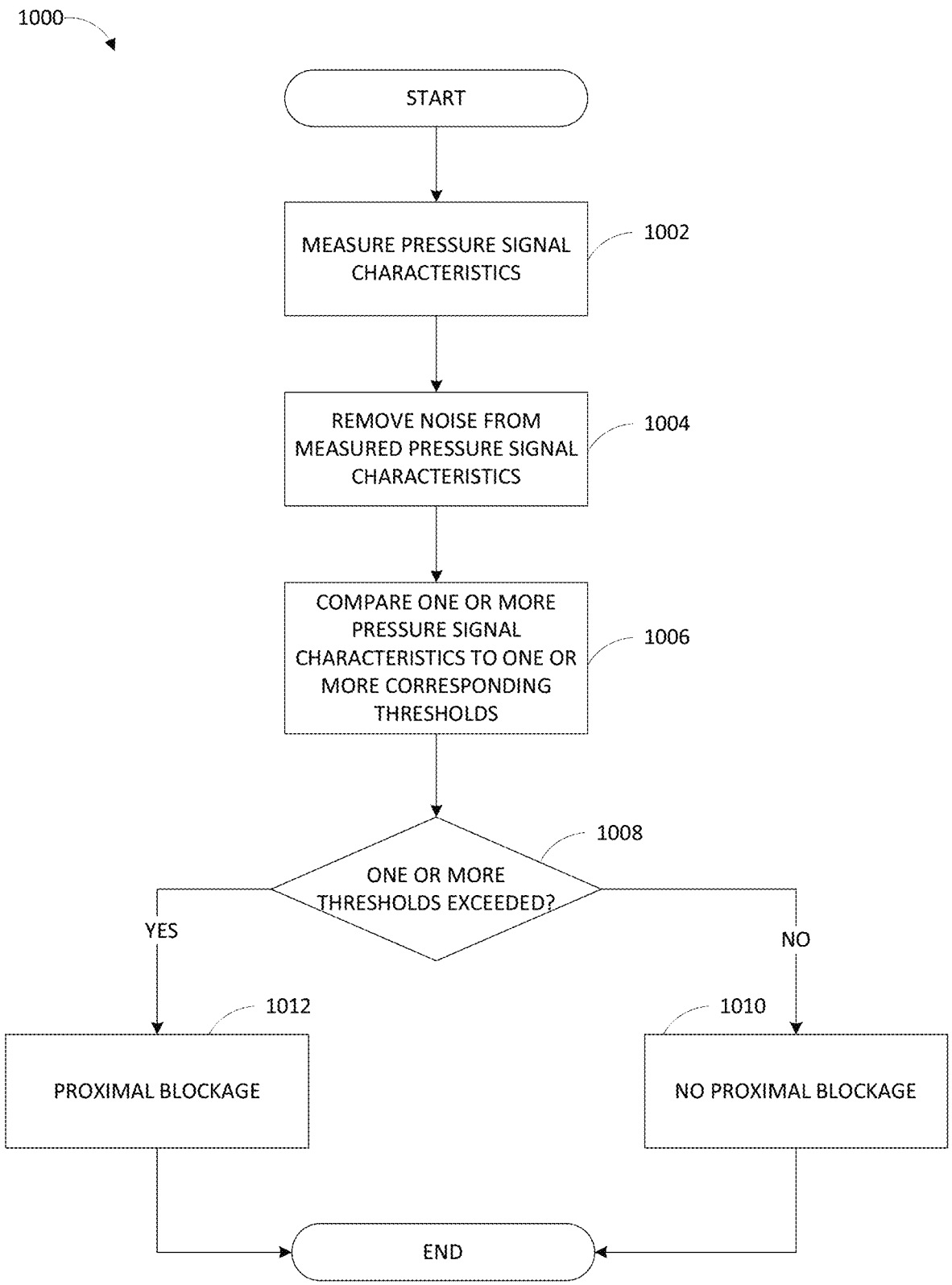
FIG. 10 illustrates a process of detecting proximal blockages according to some embodiments.

FIG. 10 illustrates a process 1000 of detecting proximal blockages according to some embodiments. The process 1000 can be implemented by a controller of processor. The process 1000 measures one or more pressure signal characteristics in block 1002. For example, pressure signal magnitude, frequency, etc. can be measured. In block 1004, the process 1000 removes noise from the one or more measured pressure signal characteristics. For example, the pressure signal can be low pass filtered. In block 1006, the process 1000 compares the one or more pressure signal characteristics to one or more thresholds. If in block 1008 the process 1000 determines that the one or more thresholds have been satisfied (e.g., exceeded), the process transitions to block 1012 where it determines that there is a proximal blockage (e.g., due to the canister being full). The process 1000 can activate one or more alarms or indicators. If in block 1008 the process 1000 determines that the one or more thresholds have not been satisfied (e.g., not exceeded), the process transitions to block 1010 where it determines that there is no proximal blockage. In some embodiments, the process 1000 can use hysteresis in block 1008. For example, the process 1000 can transition to block 1012 provided that a threshold has been met (e.g., exceeded) for a duration or period of time. In some embodiments, the one or more thresholds utilized by the process 1000 can be selected to determine canister (or dressing) pre-full condition and/or a particular level of exudate in the canister (or dressing). Process 1000 can be implemented by systems with canisters or by canisterless systems.

In some embodiments, canister (or dressing) full condition can be detected as follows. A plurality of pressure sensor readings, each performed over a time duration (e.g., 2 seconds or any other suitable duration which may be vary between sample periods), are collected. A number of readings of the plurality of readings, such as 25 sample periods out of 30 or any other suitable number, are checked to determine if each indicates that the canister is full. This can performed by determining maximum and minimum pressure values captured over the time duration of a particular sample period. The values can be voltage values, current values, or any other suitable values that correspond to pressure. A difference between maximum and minimum values for a particular sample period corresponds to peak-to-through pressure (which is indicative of change in pressure pulse amplitude). If it is determined that the peak-to-through pressure for a particular sample period exceeds a threshold pressure value, then the particular sample period indicates that the canister is full.

The threshold value can be any suitable pressure threshold, such as a value selected or determined based on the negative pressure setpoint and the current level of activity of the pump, which as explained above can be determined using a tachometer average (such as averaged tachometer readings or any other suitable measure of the flow rate). For example, threshold values listed in Table 1 can be used for comparing to peak-to-through pressure. These values correspond to a particular pump motor and particular pressure sensor.

TABLE 6

Threshold values for detecting canister full condition

| Setpoint (in mmHg) | Tachometer Frequency (in Hz) | | | Peak-to-Through Pressure (in mV) | | |
|---|---|---|---|---|---|---|
| | Low | Med | High | Low | Med | High |
| 25 | 17 | 25 | <25 | 50 | 110 | 215 |
| 40 | 23 | 35 | <35 | 75 | 135 | 220 |
| 50 | 30 | 50 | <50 | 90 | 175 | 225 |
| 60 | 30 | 55 | <55 | 80 | 185 | 225 |
| 70 | 40 | 60 | <60 | 115 | 185 | 235 |
| 80 | 40 | 60 | <60 | 100 | 165 | 235 |
| 90 | 45 | 65 | <65 | 110 | 170 | 235 |
| 100 | 45 | 65 | <65 | 105 | 165 | 235 |
| 120 | 45 | 75 | <75 | 105 | 175 | 235 |
| 140 | 50 | 85 | <85 | 110 | 190 | 235 |
| 160 | 60 | 90 | <90 | 110 | 165 | 220 |
| 180 | 75 | 100 | <100 | 130 | 165 | 220 |
| 200 | 75 | 100 | <100 | 125 | 155 | 210 |

Canister full determination can be performed on a sliding window basis. For example, a sliding window of 25 out of 30 sample periods can be analyzed and if 25 sample periods are determined to indicate that the canister is full, the pump concludes that the canister (or dressing) is full. Assuming that the sample period is 2 seconds, using a sliding window of 25 out of 30 sample periods effectively results in determining whether change in pressure pulse amplitude exceeds the threshold for 60 seconds. If the tachometer average becomes greater than a leak threshold (e.g., flow rate associated with presence of a leak in the flow path) or canister pressure (as measured by a pressure sensor) becomes less than a low vacuum pressure threshold (e.g., flow rate associated with a low vacuum condition in the flow path), canister full detection can be suspended or terminated. For example, if a sliding window of 25 out of 30 sample periods with each sample period having duration of 2 seconds in used, 60 second timer for canister full detection can be reset when it has been determined that the tachometer average becomes greater than the leak threshold or canister pressure becomes less than the low vacuum pressure threshold. This can prevent generation of unnecessary and undesirable alarms.

Alternatively or additionally, canister full condition can be detected if a single sample period indicates that the canister is full. However, performing canister full detection using a plurality of sample periods can mitigate the effects of one or more transient conditions in the fluid flow path or one or more errant pressure readings. Alternatively or additionally, canister full detection can be performed by measuring the frequency of detected pressure signal and comparing the measured frequency to one or more suitable thresholds.

In some embodiments, additional or alternative mechanisms can be used for detecting proximal blockages. One or more additional pressure sensors can be used to measure differential pressure across the canister (e.g., at the canister inlet and outlet). One or more additional conduits (e.g., dual lumens) can be used to inject a signal through one lumen for detection by another lumen. Flow rate can be measured directly or indirectly and used for canister blockage detection. A bias leak can be introduced into the flow path and maintained such that flow rate dropping below the bias leak rate indicates a presence of a blockage in the flow path. Optical sensors, ultrasonic sensors, and/or weight sensors can be used to determine the level of exudate in the canister (or dressing). Lasers can also be used. One or more sensors that are not related to measuring pressure and/or flow, such as a capacitive sensor or a strain gauge, can be used.

In some embodiments, temporary blockages caused by slugs or boluses of fluid in tubes and/or lumens are detected by turning off the pump and monitoring the pressure change in the fluid flow path. The pump can be turned off for a short duration of time as to not affect the operation of the system. Presence of temporary blockages in the system due to boluses of fluid can cause a detectable difference in pressure decay in the device including a discontinuous "stair and risers" pattern in a system with a distal leak. Such discontinuous decaying pattern may be due to boluses of fluid moving through the fluid flow path and arriving at the canister inlet, which can suddenly change the volume seen by the pressure sensor (and the canister or the dressing). When boluses of fluid are not present, a more continuous decaying pattern may be is observed. In certain embodiments, when the discontinuous "stairs and risers" pattern is detected, the system can increase the level of vacuum produced by the pump to clear the boluses. An alarm can be asserted if the tubes and/or lumens cannot be cleared.

In some embodiments, one or more flow sensors and/or flow meters can be used to directly measure the fluid flow. In some embodiments, the system can utilize one or more of the foregoing flow rate monitoring techniques. The system can be configured to suitably arbitrate between flow rates determined using multiple flow rate monitoring techniques if one or more such techniques are executed in parallel. In certain embodiments, the system execute one of the techniques, such as the flow rate determination based on the pump speed, and utilize one or more other techniques as needed. In various embodiments, the system can utilize one or more other techniques in cases the determined flow rate or flow path condition is perceived to be inaccurate or unreliable. In some embodiments, the system can utilize one or more of the techniques to detect a sudden change in a flow rate suggesting change to the dressing leak characteristics (e.g., a greater flow indicates the development of a leak and a lesser flow indicating a sudden restriction or blockage).

OTHER VARIATIONS

Any value of a magnitude, frequency, threshold, limit, duration, etc. provided herein and/or illustrated in the figures is not intended to be absolute and, thereby, can be approximate. In addition, any magnitude, frequency, threshold, limit, duration, etc. provided herein and/or illustrated in the figures can be fixed or varied either automatically or by a user. Moreover, any value of a magnitude, frequency, threshold, limit, duration, etc. provided herein and/or illustrated in the figures is illustrative and can change depending on an embodiment. For example, the values provided in the tables (Tables 1-5) can vary depending on canister (or dressing) volume, sensor range, etc. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed (such as the process illustrated in FIG. 10), may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound therapy apparatus comprising:
    a negative pressure source configured to provide negative pressure, via a fluid flow path, to a wound covered by a wound dressing;
    a canister configured to be positioned in the fluid flow path and to store exudate aspirated from the wound;
    at least one pressure sensor configured to monitor a pressure in the fluid flow path; and
    a controller configured to:
        distinguish between a blockage in the fluid flow path and an amount of exudate in the canister reaching a threshold level of fluid, wherein the blockage in the fluid flow path and the amount of exudate in the canister reaching the threshold level of fluid cause a decrease in a level of activity of the negative pressure source;
        detect the blockage in the fluid flow path responsive to the level of activity of the negative pressure source satisfying a threshold level of activity;
        detect a leak in the fluid flow path responsive to a pressure difference across a flow restrictor positioned in the fluid flow path satisfying a leak threshold;
        perform a first action responsive to detection of the blockage in the fluid flow path;
        perform a second action responsive to detection that the amount of exudate in the canister has reached the threshold level of fluid; and
        perform a third action responsive to detection of the leak in the fluid flow path.

2. The wound therapy apparatus of claim 1, wherein:
    the first action comprises activating a blockage alarm;
    the second action comprises activating a canister full alarm; and
    the third action comprises activating a leak alarm.

3. The wound therapy apparatus of claim 1, wherein the controller is further configured to monitor activity of the negative pressure source using a tachometer.

4. The wound therapy apparatus of claim 1, wherein the at least one pressure sensor comprises first and second pressure sensors configured to monitor the pressure difference across the flow restrictor.

5. The wound therapy apparatus of claim 1, wherein the controller is configured to detect the blockage in the fluid flow path responsive to the level of activity of the negative pressure source satisfying the threshold level of activity over at least a threshold time duration.

6. The wound therapy apparatus of claim 1, wherein the threshold level of fluid is indicative of the canister being full, and wherein the controller is further configured to determine that the amount of exudate in the canister has reached the threshold level of fluid indicative of the canister being full responsive to a determination that a magnitude of the pressure satisfies a pressure threshold.

7. The wound therapy apparatus of claim 6, wherein the controller is further configured to determine the pressure threshold from the level of activity of the negative pressure source and a negative pressure setpoint.

8. A method of operating a wound therapy apparatus comprising:
    activating a negative pressure source to provide negative pressure to a wound covered by a wound dressing through a fluid flow path fluidically connecting the negative pressure source with the wound dressing and a canister;

distinguishing between a blockage in the fluid flow path and an amount of exudate in the canister reaching a threshold level of fluid, wherein the blockage in the fluid flow path and the amount of exudate in the canister reaching the threshold level of fluid cause a decrease in a level of activity of the negative pressure source;

at a first time:
   detecting the blockage in the fluid flow path responsive to the level of activity of the negative pressure source satisfying a threshold level of activity; and
   performing a first action responsive to detecting the blockage in the fluid flow path;

at a second time, performing a second action responsive to detecting that the amount of exudate in the canister has reached the threshold level of fluid; and at a third time:
   detecting a leak in the fluid flow path responsive to a pressure difference across a flow restrictor positioned in the fluid flow path satisfying a leak threshold; and
   performing a third action responsive to detection of the leak in the fluid flow path, wherein the method is performed under control of a controller.

9. The method of claim 8, wherein:
the first action comprises activating a blockage alarm;
the second action comprises activating a canister full alarm; and
the third action comprises activating a leak alarm.

10. The method of claim 8, wherein:
the first action comprises activating a blockage alarm;
the second action comprises interrupting provision of the negative pressure; and
the third action comprises activating a leak alarm.

11. The method of claim 8, further comprising monitoring activity of the negative pressure source using a tachometer.

12. The method of claim 8, further comprising detecting the blockage in the fluid flow path responsive to the level of activity of the negative pressure source satisfying the threshold level of activity over at least a threshold time duration.

13. The method of claim 8, wherein the threshold level of fluid is indicative of the canister being full, and wherein the method further comprises determining that the amount of exudate in the canister has reached the threshold level of fluid indicative of the canister being full responsive determining that a magnitude of pressure satisfies a pressure threshold.

14. The method of claim 13, further comprising determining the pressure threshold from the level of activity of the negative pressure source and a negative pressure setpoint.

15. The method of claim 8, wherein the leak in the fluid flow path is detected responsive to the pressure difference across the flow restrictor satisfying the leak threshold over at least a threshold time duration.

16. The wound therapy apparatus of claim 1, wherein the leak in the fluid flow path is detected responsive to the pressure difference across the flow restrictor satisfying the leak threshold over at least a threshold time duration.

17. The wound therapy apparatus of claim 1, wherein the threshold level of fluid is indicative of the canister not yet being full.

18. The wound therapy apparatus of claim 16, wherein the threshold level of fluid is indicative of the canister being no more than 80% full.

19. The wound therapy apparatus of claim 16, wherein the threshold level of fluid is indicative of the canister being no more than 95% full.

20. The wound therapy apparatus of claim 1, wherein:
the first action comprises activating a blockage alarm;
the second action comprises interrupting provision of the negative pressure; and
the third action comprises activating a leak alarm.

* * * * *